United States Patent

Roth et al.

Patent Number: 5,545,535
Date of Patent: Aug. 13, 1996

[54] FLUORESCENT ASSAY FOR BACTERIAL GRAM REACTION

[75] Inventors: Bruce L. Roth, Corvallis; Paul J. Millard; Stephen T. Yue, both of Eugene; K. Sam Wells, Veneta; Richard P. Haugland, Eugene, all of Oreg.

[73] Assignee: Molecular Probes, Inc., Eugene, Oreg.

[21] Appl. No.: 146,328

[22] Filed: Nov. 1, 1993

Related U.S. Application Data

[63] Continuation-in-part of Ser. No. 90,890, Jul. 12, 1993, Pat. No. 5,436,134, which is a continuation-in-part of Ser. No. 47,683, Apr. 13, 1993, abandoned.

[51] Int. Cl.$^6$ .............. C12Q 1/04; C12Q 1/68; G01N 33/00; C07H 1/00
[52] U.S. Cl. .............. 435/34; 435/6; 435/29; 435/39; 435/4; 436/94; 436/800; 436/172; 536/26.73; 536/1.11; 536/25.6
[58] Field of Search .............. 435/34, 29, 4, 435/14, 6, 33, 32, 39; 436/94, 800, 172; 536/27, 26.73, 1.11, 25.6; 558/161

[56] References Cited

U.S. PATENT DOCUMENTS

| | | | |
|---|---|---|---|
| 4,126,516 | 11/1978 | Messing et al. | 195/103.5 |
| 4,190,328 | 2/1980 | Levine et al. | 350/320 |
| 4,225,669 | 9/1980 | Melnick et al. | 435/29 |
| 4,508,821 | 4/1985 | Mansour et al. | 435/34 |
| 4,544,546 | 10/1985 | Wang et al. | 424/7.1 |
| 4,639,421 | 1/1987 | Sage, Jr. | 435/34 |
| 4,665,024 | 5/1987 | Mansour et al. | 435/34 |
| 4,883,867 | 11/1989 | Lee et al. | 536/28 |
| 4,937,198 | 6/1990 | Lee et al. | 436/94 |
| 4,997,928 | 3/1991 | Hobbs, Jr. | 435/6 |
| 5,057,413 | 10/1991 | Terstappen et al. | 435/6 |
| 5,137,810 | 8/1992 | Sizemore et al. | 435/7.32 |

FOREIGN PATENT DOCUMENTS

| | | |
|---|---|---|
| 0410806A1 | 1/1991 | European Pat. Off. |
| 0453197A1 | 10/1991 | European Pat. Off. |
| 2074340 | 10/1981 | United Kingdom. |

OTHER PUBLICATIONS

Kudinova, et al., Chemical Abstracts 93:241180j (1993).
Kudinova, et al. Khim. Geterotsikl. Soedin. 7, 903 (1980).

(List continued on next page.)

*Primary Examiner*—John Kight, III
*Assistant Examiner*—Louise N. Leary
*Attorney, Agent, or Firm*—Allegra J. Helfenstein; Anton E. Skaugset

[57] ABSTRACT

The invention relates to a method of analyzing a sample thought to contain bacteria using an aqueous solution comprising one or more fluorescent dyes: a fluorescent dye of formula I, a fluorescent dye of formula II, a fluorescent dye of formula III, and a fluorescent dye of formula IV. Each of the dyes differ each from the other in their affinity for nucleic acids and in their spectral response to different types of bacteria in the sample. The first three dyes are nucleic acid stains and the fourth dye is a fluorescent reagent that binds selectively to cell surface components. The fluorescent dyes of formula I are highly membrane-permeant cyanine dye derivatives and label all bacteria, whether live or dead, whether Gram positive or Gram negative. The dyes of formula II label only live Gram positive bacteria and label all dead bacteria, whether Gram positive or negative. The dyes of formula II bind to nucleic acids preferentially with respect to the dyes of formula I. Fluorescent formula III dyes are membrane impermeant dyes that give a fluorescent signal only in cells with compromised plasma membrane integrity, whether Gram negative or Gram positive, and have a much higher binding affinity for nucleic acids than the fluorescent dyes of either formula I or formula II. Formula IV fluorescent dyes preferentially bind to an exterior component of a bacterium. The dyes are combined with a sample suspected of containing bacteria and illuminated at an appropriate wavelength to differentiate, according to the fluorescence response, live Gram negative, dead Gram negative, live Gram positive and dead Gram positive bacteria in the sample.

20 Claims, 3 Drawing Sheets

OTHER PUBLICATIONS

Simbera, et al., Chemical Abstracts 89:112299y (1978).
Griffiths, Colour and Constitution of Organic Molecules, p. 241 Academic Press (1976).
Hamer, "The Cyanine Dyes and Related Compounds," The Chemistry of Heterocyclic Compounds, vol. 18, A Weissberger, Ed., Interscience, New York (1964).
Heterocyclic Compounds, vol. 4, R. C. Elderfield ed., John Wiley and Sons Inc., (1952) pp. 1–331.
Wawzonek, et al., J. Heterocyclic Chem., 25, 381 (1988).
Watkins, J. Chem. Soc. (1952) pp. 3059–3064.
Brinkley, Bioconj. Chem. vol. 3, pp. 1–13 (1992).
Marson, Tetrahedron, 48, 3659 (1992).
Rye, et al., Nucleic Acid Res., 20, 2083 (1992).
Matsuyama, Fems Microbiological Letters 21, 153 (1984).
Govorunov, et al., Microbiology 51, 587 (1982).
Brooker, et al., J. Am. Chem. Soc. 64, 199 (1942).
Haugland, Handbook of Fluorescent Probes and Research Chemicals (5th ed. 1992) and (1989).
J. Chem. Soc. 3059 (1952).
Sizemore, et al., Appl. Env. Microbiol. 56, 2245 (1990).

FLUORESCENT ASSAY FOR BACTERIAL GRAM REACTION

This application is a continuation-in-part of patent application Ser. No. 08/090,890, filed Jul. 12, 1993, now U.S. Pat. No. 5,436,134, which is itself a continuation-in-part of patent application Ser. No. 08/047,683, filed Apr. 13, 1993, now abandoned.

FIELD OF INVENTION

The invention relates to the staining of microorganisms. In particular, the invention relates to the use of a combination of fluorescent dyes for the determination of Gram sign in a population of bacteria, which optionally includes the determination of cell viability.

BACKGROUND OF THE INVENTION

Researchers and industrial scientists have a need to analyze cells frown mixed populations of microorganisms for Gram sign. Unfortunately, the known methods for determination of Gram sign involve the use of organic solvents, chemical fixatives (such as formaldehyde) and staining buffers containing chelating or permeabilizing agents, each of which is known to significantly affect the properties of the cell membrane and to potentially effect cell viability.

The differentiation of Gram-positive bacteria and Gram-negative bacteria has conventionally been accomplished with a multistep colorimetric staining protocol using crystal violet and a safranin O counterstain on heat fixed bacteria. This protocol typically kills the cells being tested. In U.S. Pat. No. 4,225,669, Melnick et al. disclose a method for staining suspended bacteria using a chelating agent and a nonfluorescent dye followed by an acid wash. This method also interferes with simultaneous or subsequent analysis of viability.

Similar methods using fluorescent dyes have also been developed to take advantage of the superior sensitivity afforded by fluorescence. The fluorescent dye, rhodamine 123, was observed by Matsuyama (FEMS MICROBIOLOGY LETTERS 21, 153 (1984)) to display a slight selectivity for Gram-positive bacteria (12 Gram-positive strains versus seven of 14 Gram-negative strains). U.S. Pat. No. 4,126,516 to Messing et al. discloses a method that involves culturing the microorganisms in a fluorescent lipophilic compound that is incorporated to a greater extent in the membranes of Gram negative cells, which thus become relatively more fluorescent. These methods, however, are less accurate than conventional procedures and are more labor intensive and time consuming.

The use of special staining buffers has been found to enhance the ability of several fluorescent nucleic acid dyes to stain microorganisms. Govorunov et al. (MICROBIOLOGY 51,587 (1982)) reported that the nucleic acid stain ethidium bromide is impermeant to Gram-negative *E. coli* until treated with a chelating agent such as ethylenediamine tetraacetic acid (EDTA). U.S. Pat. No. 4,508,821 to Mansour et al. (1985) uses an aqueous staining buffer comprising EDTA, as well as sodium borate, formaldehyde, and a surface active agent such as Triton X-100 to detect bacteria associated with white blood cells. Likewise, U.S. Pat. No. 4,665,024 to Mansour, et al. (1987) describes the use of ethidium bromide in combination with acridine orange or thioflavin T to distinguish Gram positive and Gram negative microorganisms, optionally using a staining buffer with EDTA as above, but the method does not reliably distinguish Pseudomonas. U.S. Pat. No. 4,639,421 to Sage (1987) discloses the use of a staining buffer containing a permeabilizing agent with the fluorescent nucleic acid dye propidium iodide in conjunction with a second fluorescent dye (acridine orange, acriflavin, quinacrine, or chrysaniline), such that Gram-positive bacteria fluoresce green and Gram-negative bacteria fluoresce orange.

None of the methods previously described for determination of Gram reaction are suitable for simultaneous or subsequent determination of viability. Separate methods using fluorescent dyes for the analysis of cell viability have been developed. Live, intact cells can be distinguished from dead cells with compromised membranes by differential staining using a cell-impermeant fluorescent dye, and a cell-permeant dye that requires an intracellular reaction for the production of fluorescence. Examples of fluorescent viability stains include fluorescein diacetate, as well as nucleic acid stains acridine orange (U.S. Pat. No. 4,190,328), calcein-AM (Ser. No. 07/783,182 (filed Oct. 26, 1991) to Haugland et al. now U.S. Pat. No. 5,314,805), DAPI and Hoechst 33342. The use of acridine orange is severely limited because of high background signal and low fluorescence enhancement upon binding to nucleic acids (about two-fold). Nucleic acids complexed with DAPI or Hoechst 33342 are only excitable with UV light, which is incompatible with some instrumentation. More importantly, the spectral properties of DAPI- or Hoechst 33342-bound DNA overlap significantly with cellular autofluorescence.

The method of the present invention provides significant advantages over conventional methods for the analysis of bacteria. This method, which allows the determination of Gram sign and cell viability either simultaneously or sequentially, is extremely sensitive, reliable and fast, requires no harsh reagents or special culturing conditions, and is applicable to a wide range of microorganisms, regardless of the source. It is useful for laboratory analysis, industrial process monitoring and environmental sampling. The method comprises a combination of one to four fluorescent dyes that determine Gram sign in mixed populations of bacteria. The dyes can be used in any combination, depending on how much is initially known about the population of microorganisms being tested.

One of the dyes of the invention, from a new family of unsymmetrical cyanine dyes, was unexpectedly found to label Gram-positive bacteria and Gram-negative bacteria, whether live or dead. Although certain unsymmetrical cyanine dyes were first described before the genetic role of nucleic acids was established (Brooker, et al., J. AM. CHEM. SOC. 64, 199 (1942)), a variety of unsymmetrical cyanine dyes have now been found to be very effective in the fluorescent staining of DNA and RNA. Patent applications have been filed on DIMERS OF UNSYMMETRICAL CYANINE DYES (Ser. No. 07/761,177 filed Sep. 16, 1991 by Yue et al.) now abandoned, UNSYMMETRICAL CYANINE DYES WITH CATIONIC SIDE CHAIN (Ser. No. 07/833,006 filed Feb. 8, 1992 by Yue, et al.), now U.S. Pat. No. 5,321,130 and DIMERS OF UNSYMMETRICAL CYANINE DYES CONTAINING PYRIDINIUM MOIETIES (filed Apr. 5, 1993 by Yue et al.) (all three patent applications incorporated by reference). U.S. Pat. Nos. 4,554,546 (to Wang, et al. 1985) and 5,057,413 (to Terstappen et al. 1991) disclose use of similar derivatives of thioflavins as nucleic acid stains. U.S. Pat. No. 4,937,198 (to Lee et al. 1990) discloses a fluorescent nucleic acid stain that preferentially stains the nucleic acids of bloodborne parasites with little staining of nucleated blood cells. Closely related lower alkyl (1–6 carbons) substituted unsymmetrical cyanine dyes, exemplified by thiazole orange, are disclosed in U.S. Pat. No. 4,883,867 to Lee et al. as having particular advantages in reticulocyte analysis.

It was found that the attachment of bulkier, cyclic structures to the parent unsymmetrical cyanine dye resulted in a number of unexpected advantages for this family of dyes. For example, although bulkier, many of the new dyes more quickly penetrate the cell membranes of a wider variety of cell types, including both Gram-positive and Gram-negative bacteria and eukaryotic cells, as described in Copending Application CYCLIC-SUBSTITUTED UNSYMMETRICAL CYANINE DYES, Ser. No. 08/090,890, filed Jul. 12, 1993, incorporated by reference. Direct comparison of the rate of uptake with known dyes such as thiazole orange and its alkylated derivatives, shows enhanced uptake of many of the new compounds (Table 5, FIG. 2). Moreover, bacteria stained with selected unsymmetrical dyes with cyclic substituents exhibit greater than tenfold more fluorescence than bacteria stained with thiazole orange (Table 3). In addition, the quantum yield of the dyes of this family are unexpectedly better than that of thiazole orange (Table 1). Furthermore, by simple synthetic modification, a family of dyes having absorption and emission spectral properties that cover most of the visible and near-infrared spectrum can be prepared. The dyes of the invention have one or more of these advantageous properties. These features overcome the limitations imposed by thiazole orange and other unsymmetrical cyanine dyes for staining the nucleic acids of living cells. The superior properties exhibited by these dyes were neither anticipated nor obvious in view of the known unsymmetrical cyanine dyes.

A second fluorescent dye used in the invention was unexpectedly discovered to selectively stain the nucleic acids of live Gram-positive bacteria as well as nucleic acids of dead Gram-positive and dead Gram-negative bacteria with a red fluorescence. Two similar dyes, ethidium bromide and propidium iodide, are known to be relatively impermeant to viable cells, see e.g. Haugland, HANDBOOK OF FLUORESCENT PROBES AND RESEARCH CHEMICALS (5th ed. 1992) and (1989) (both editions incorporated by reference), and have been used to distinguish Gram positive and Gram negative bacteria, e.g. U.S. Pat. No. 4,665,024 to Mansour, et al. (1987) supra (ethidium bromide stained several Gram positive and one Gram negative bacterial species) and U.S. Pat. No. 4,639,421 to Sage (1987) supra (propidium iodide combined with another dye in a staining buffer used to distinguish Gram negative and Gram positive bacteria). Although propidium also contains an alkyl substituent, its substituent contains a positive charge and it is even less membrane-permeant than ethidium. The second dye of the invention contains an alkyl substituent that is much longer than the ethyl group of ethidium. It stains live Gram positive cells without the use of chelators, fixatives, or other permeabilizing reagents, but does not stain live Gram negative cells. This provides significant advantages since the permeabilizing agents compromise the membrane integrity, resulting in ambiguous results with regard to cell viability. Although the second dye used for the invention also lightly stains some Gram negative organisms when used alone, the combination of dyes, as well as experience with the technique, assures that a correct result is obtained. The synthesis of the second fluorescent dye was described in J. CHEM SOC. 3059 (1952), but the reference neither discloses nor suggests the use of this compound as a nucleic acid stain as proposed in the present invention.

The third dye used in the method is an unsymmetrical cyanine dye derivative, such as those commercially available under the trademarks YOYO™, TOTO™, TO-PRO™, YO-PRO™, POPO™ and BOBO™ from Molecular Probes, Inc., Eugene, Oregon and covered under pending patents described above. As described in Molecular Probes' catalogue, HANDBOOK OF FLUORESCENT PROBES AND RESEARCH CHEMICALS Set 31 (5th ed. 1992), supra, the unsymmetrical cyanine dyes are membrane-impermeant dyes that can be used for probing membrane integrity, which is related to cell viability. These dyes, however, displace both the other nucleic acid stains of the invention from a nucleic acid complex. Thus, for example, in a population containing only Gram positive organisms, dead Gram positive organisms can be distinguished from live Gram positive organisms when the third dye is combined with the second dye of the invention. Furthermore, dead Gram negative bacteria and dead Gram positive bacteria can be distinguished from live Gram negative bacteria and from live Gram positive bacteria when all three dyes of the invention are used. These unexpected advantages are neither disclosed nor obvious from the HANDBOOK reference.

The fourth dye of the invention is a fluorescent reagent that binds selectively to the surface of a bacterium. This reagent is typically a protein, such as an antibody specific for cell surface components or a lectin such as wheat germ agglutinin. Although fluorescent lectins are known to bind to the outside of Gram positive microorganisms and not Gram negative microorganisms (e.g. U.S. Pat. No. 5,137,810 to Sizemore, et al. (1992) (incorporated by reference) and Sizemore, et al., APPL. ENV. MICROBIOL. 56, 2245 (1990)), and a variety of colored and fluorescent derivatives thereof have long been known, wheat germ agglutinin alone cannot be used to distinguish between live and dead Gram positive cells. Furthermore, since Gram negative organisms, whether live are dead, would only be indicated by lack of staining, wheat germ agglutinin alone does not affirmatively indicate whether any Gram negative organisms are present, particularly if they are present in minute quantities. Moreover, the preparation of the lectin-dye solution discovered for this invention gives unexpectedly superior results, so that the dye can be used without the wash step required by the Sizemore patent. The particular combination of dyes disclosed in this invention is neither anticipated nor obvious from known applications of fluorescent lectin derivatives.

SUMMARY OF THE INVENTION INCLUDING DESCRIPTION OF PREFERRED EMBODIMENTS

Figure 1:
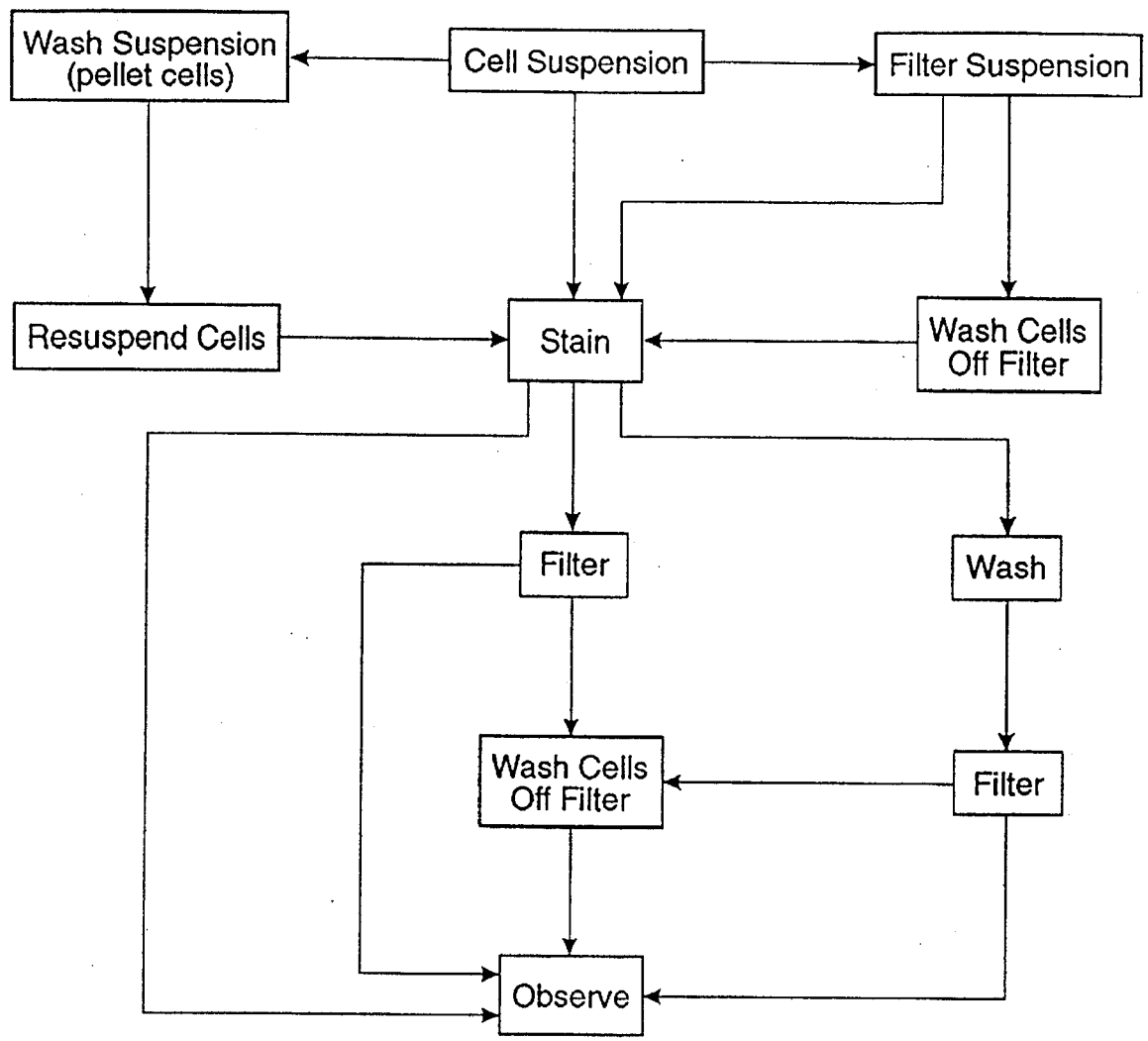
FIG. 1: Flow Chart of Alternative Pathways for Concentrating and Staining Bacteria: An illustration of different protocols that can be used to prepare bacteria for observation.

The invention relates to a method of analyzing a sample thought to contain bacteria using an aqueous solution comprising one or more fluorescent dyes. Using fluorescent detection techniques, and optionally using transmitted light microscopy, this method is used to determine the Gram reaction of bacterial cells and optionally the viability of the bacteria. Although the preferred method requires an aqueous dye solution comprising at least three different dyes, limited Gram reaction and viability determinations can be made with dye solutions comprising fewer dyes, particularly when transmitted light observations are included along with the detection of fluorescent signals. The fluorescence properties of the stains used in this procedure enhance the sensitivity of the technique by allowing the detection of individual organisms in complex mixtures. In one aspect of the invention, the technique combines three specific nucleic acid stains with a surface label to simultaneously provide an accurate measure of plasma membrane integrity and Gram reaction of bacteria in a sample.

The bacteria sample is any sample of solid or liquid thought to contain bacteria. Typically the sample is a bodily fluid such as blood, urine, peritoneal fluid, spinal fluid, or other similar fluids. Alternatively the sample is a fermentation medium such as from a biological reactor or food fermentation process such as brewing. Other sources for samples include water, for example inline, industrial, or outdoor sources; or surface washes of materials, e.g. food surfaces; or small amounts of solids such as retentates, scrapes, and smears; or liquid growth medium in which microorganisms have been introduced for culturing.

The sample typically contains Gram positive cells, Gram negative cells, or a mixture of both. Gram positive ($G^+$) bacteria are those that give a positive Gram stain, including but not limited to Bacillus, Lactobacillus, Micrococcus, Streptococcus, Clostridium, Staphylococcus, and Mycobacterium, among others. Gram negative ($G^-$) bacteria are those that are negative for the Gram stain, including but not limited to Escherichia, Enterobacter, Salmonella, Pseudomonas, Shigella, Klebsiella, Haemophilus, Neisseria, Proteus, Vibrio, Campylobacter, and Yersinia, among others.

The Gram positive or Gram negative cells may be a mixture of both viable and dead cells. As used throughout this document, the term "viable" is used to describe those cells with an intact cell membrane. While there is not an exact equivalence between an intact cell membrane and the term "viability" (technically defined as the ability of a cell to maintain its existence), it is common to refer to cells that have intact membranes as "viable" cells. Those cells where the cell membrane has been irreversibly disrupted are "dead" cells or "membrane-compromised" cells. Loss of the protective cell membrane results in loss of cell structure, loss of critical intracellular contents, loss of essential ionic gradients and loss of electrical potential. The inevitable result of a major loss of membrane integrity is cell death. It should be obvious that where cell death results in the loss of all intracellular nucleic acids, none of the nucleic acid stains of the invention will label the cellular debris that remains.

For use in the method of this invention, the bacteria sample is optionally in suspension or is immobilized on a solid or semisolid support. In one embodiment of the invention, the bacteria sample is in suspension on a microscope slide or in a specialized container needed for an instrumentation detection method such as in a cuvette or in a microtiter plate (e.g. 96 well titer plate). Alternatively, the bacteria sample is adhered to a microscope slide using a cell adhesive solution such as poly-L-lysine or is attached to a filter as a retained residue or retentate.

The bacteria sample is combined with an aqueous or partially aqueous dye solution. Depending on the type of sample and characteristics of the bacteria population thought to be contained in the sample, the sample is added to the dye solution or the dye solution is added to the bacteria sample (see flow chart, FIG. 1). Different pathways are selected as required, based on the type of sample, the bacterial species, the preferred staining protocol, or the detection technique. For example, a filter containing a retentate removed from a liquid sample such as water can be placed in the aqueous dye solution, allowing the retentate to incubate in the dye solution (Examples 20, 22). Alternatively, where the bacteria sample is placed on a slide or in a specialized container, the aqueous dye solution can be added to the slide or container. A mixture of dyes can be added in one step or in a series of steps.

The aqueous dye solution of the invention comprises one or more of the following dyes or stains: a fluorescent dye of formula I, a fluorescent dye of formula II, a fluorescent dye of formula III, and a fluorescent dye IV. Each of the dyes differ each from the other in their affinity for nucleic acids and in their spectral response to different types of bacteria in the sample. The first three dyes are nucleic acid stains and the fourth dye is a fluorescent reagent that binds selectively to cell surface components. Each of the nucleic acid stains used for the invention is lightly colored or colorless and is virtually non-fluorescent when diluted in aqueous solution according to the method of the invention. When the fluorescent nucleic acid stains of the invention bind with intracellular nucleic acid polymers such as DNA and RNA, the resultant dye-nucleic acid complex becomes extremely fluorescent. The surface label that only stains externally is distinguishable from the nucleic acid stains that generally stain intracellularly. When a surface dye is used in combination with one or more nucleic acid stains, a "bullseye" pattern of staining is seen—i.e. a brightly stained interior within an exterior ringstain. Because of the difference in staining, the surface label is distinguishable from any nucleic acid stain when they are used in combination. Where more than one nucleic acid stain is used, each dye complexed with intracellular nucleic acids has an emission spectrum that is detectably different from the emission spectrum of the other dyes, resulting in a distinct signal for different categories of organisms. Preferably, the surface label also has an emission spectrum that is detectably different from that of the other dyes. Thus, the appearance of the stained bacteria indicates whether or not the bacteria present in the sample are viable, and also indicates the Gram reaction of the bacteria in the sample. Preferably the excitation spectrum of each dye or dye-nucleic acid complex overlaps the excitation spectrum of the other dye(s). More preferably, each dye complexed with nucleic acids has an excitation maximum between about 480 nm and 510 nm. Most preferably, each dye or dye-complex also excites in the UV between about 300 nm and 365 nm.

Formula I Dyes

The fluorescent dyes of formula I are highly membrane-permeant cyanine dye derivatives that label all bacteria, whether Gram positive or Gram negative, whether live or dead. Typically, the dyes of formula I combine with intracellular nucleic acids to give a green fluorescence. When excited at a wavelength between about 300 nm and about 500 nm, the dyes complexed with nucleic acids have an emission maximum between about 500 and about 610 nm (see Table 1). Preferred formula I dyes complexed with nucleic acids have an emission maximum of between about 500 nm and about 535 nm, resulting in a true green fluorescent signal inside bacteria. Formula I dyes that are not monomethine dyes (vide infra) do not have the preferred spectral characteristics, but could still be useful in conjunction with a dye of formula III that has a green fluorescent signal.

The fluorescent dyes of formula I include the family of unsymmetric cyanine dyes of the formula

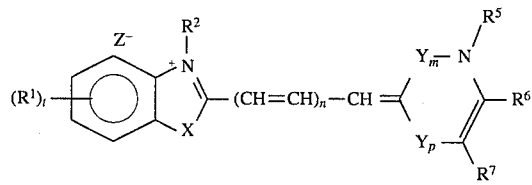

The formula I dye can be considered in three parts: 1) A first heterocyclic ring system that is a substituted benzazolium ring system, 2) a linking methine bridge and 3) a second heterocyclic ring system that is a pyridinium or quinolinium ring system, that contains at least one cyclic substituent (an OMEGA).

An OMEGA is a saturated or unsaturated, substituted or unsubstituted, cyclic substituent that has a total of 2–16 ring carbon atoms in 1–2 alicyclic, heteroalicyclic, aromatic, or heteroaromatic rings containing 1–4 heteroatoms (wherein the hetero atoms are O, N or S) that is directly bonded to the pyridinium or quinolinium ring system by a single bond. OMEGAs that are alicyclic ring systems may be either linked or fused. Examples of OMEGA are substituted or unsubstituted cyclohexyls, cyclohexenyls, morpholinos, and piperidinyls. Examples of OMEGA that are aromatic include substituted or unsubstituted naphthyls, phenyls, thienyls, benzothiazolyls, furanyls, oxazolyls, benzoxazolyls, and pyridinyls. Substituents on OMEGA are independently hydrogen, halogen, alkyl, perfluoroalkyl, amino, alkylamino, dialkylamino, alkoxy or carboxyalkyl, each alkyl having 1–6 carbons. Preferred embodiments of OMEGA are substituted or unsubstituted naphthyl, phenyl, thienyl, morpholino, and cyclohexyl, more preferably substituted or unsubstituted phenyl.

Although $R^1$ on the benzazolium ring system is usually H, incorporation of a non-hydrogen substituent $R^1$ can be used to fine tune the absorption and emission spectrum of the resulting dye. For instance when $R^1$ is methoxy (dye 770) the dye's absorption spectrum shifts ~12 nm and its emission spectrum when bound to DNA shifts ~18 nm relative to the comparable compound (dye 63) where $R^1$ is H (Tables 2 and 3). The benzazole may contain more than one substituent $R^1$, which may be the same or different (t=1–4). Each $R^1$ is optionally an alkyl group having from 1–6 carbons; or a trifluoromethyl; or a halogen; or $-OR^8$, $-SR^8$ or $-(NR^8R^9)$ where $R^8$ and $R^9$, which can be the same or different, are independently H or alkyl groups having 1–6 carbons; or 1–2 alicyclic, heteroalicyclic, aromatic, or heteroaromatic rings having a total of 3–16 ring atoms (wherein the hetero atoms are O, N or S); or $R^8$ and $R^9$ taken in combination are $-(CH_2)_2-L-(CH_2)_2-$ where $L=-O-$, $-NR^{10}$, $-CH_2-$ or a single bond where $R^{10}$ is H or an alkyl group having 1–6 carbons. Typically, the compound contains no more than one $R^1$ is not H.

The substituent $R^2$ is an alkyl group having 1–6 carbons, preferably methyl or ethyl, more preferably methyl.

The counterion $Z^-$ is a biologically compatible ion that is stable and synthetically accessible. As used herein, a substance that is biologically compatible is not toxic as used, and does not have a substantially deleterious effect on biomolecules. Examples of $Z^-$ include, among others, chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred $Z^-$ counterions are chloride, iodide, perchlorate and various sulfonates.

X is one of O, S, Se or $NR^{15}$, where $R^{15}$ is H or an alkyl group having 1–6 carbons. Alternatively, X is $CR^{16}R^{17}$, where $R^{16}$ and $R^{17}$, which may be the same or different, are independently H or alkyl groups having 1–6 carbons, or the carbons of $R^{16}$ and $R^{17}$ taken in combination complete a five or six membered saturated ring. In preferred embodiments, $R^{16}$ and $R^{17}$ are methyls.

The methine bridge consists of 1, 3 or 5 methine (—CH=) groups that bridge the benzazolium portion of the molecule and the pyridinium portion in such a way as to permit extensive electronic delocalization. When n=0, the dyes are unsymmetrical monomethine dyes; when n=1, the dyes are trimethine dyes; when n=2, the dyes are pentamethine dyes. It has been recognized from studies involving similar compounds that the number of methine groups between the heteroaromatic rings has a considerable influence on the spectral properties of the dye (Griffiths, COLOUR AND CONSTITUTION OF ORGANIC MOLECULES, pp. 241 Academic Press (1976)).

The N-bound substituent $R^5$ is an alkyl, alkenyl, polyalkenyl, alkynyl or polyalkynyl group having 1–6 carbons; or $R^5$ is an OMEGA. Most commonly $R^5$ is an OMEGA.

The pyridinium or quinolinium ring system contains a ring fragment Y that is $-CR^3=CR^4-$, with subscripts p and m equal to 0 or 1, such that p+m=1. For all embodiments, the ring contains a 6 membered pyridinium-based heterocycle according to one of these formulations:

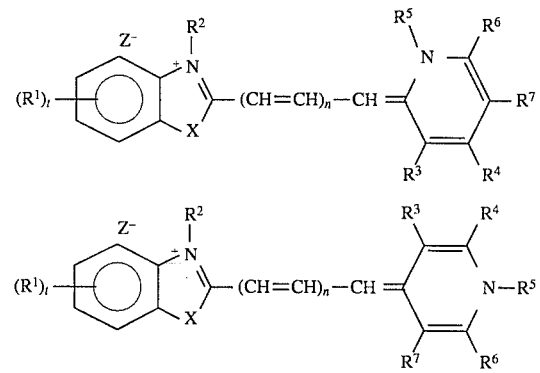

In preferred embodiments of the invention, m=1 and p=0 (4-pyridinium).

The substituents on the second heterocyclic ring system, $R^3$, $R^4$, $R^6$ and $R^7$, may be the same or different and are independently H; or an alkyl, alkenyl, polyalkenyl, alkynyl or polyalkynyl group having 1–6 carbons; or a halogen; or $-OR^8$, $-SR^8$, $-(NR^8R^9)$, as defined previously; or $-OSO_2R^{19}$ where $R^{19}$ is alkyl having 1–6 carbons, or perfluoroalkyl having 1–6 carbons, or aryl; or an OMEGA (defined above); or $R^6$ and $R^7$ taken in combination are $-(CH_2)_v-$ where v=3 or 4, forming a fused 5 or 6 membered ring; or $R^6$ and $R^7$, taken in combination form a fused 6 membered aromatic ring.

Where $R^6$ and $R^7$ taken in combination form a fused 6 membered aromatic ring, embodiments of this invention are quinolinium derivatives containing a fused aromatic ring according to the formula

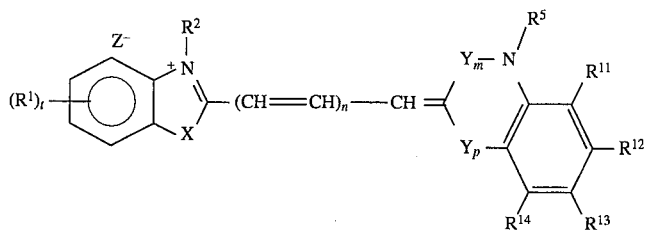

where ring substituents $R^{11}$, $R^{12}$, $R^{13}$, and $R^{14}$ may be the same or different, and are independently H; or an alkyl, alkenyl, polyalkenyl, alkynyl or polyalkynyl group having 1–6 carbons; or a halogen; or —$OR^8$, —$SR^8$, —($NR^8R^9$), where $R^8$ and $R^9$ are as defined previously; or —$OSO_2R^{19}$ where $R^{19}$ is alkyl having 1–6 carbon, or perfluoroalkyl having 1–6 carbons, or aryl; or an OMEGA. A preferred embodiment of the invention is a quinolinium wherein m=1 and p=0 (4-quinolinium).

For all embodiments of the invention, one or more of the substituents of the pyridinium or quinolinium ring system must be an OMEGA. Preferably, one or two substituents are OMEGAs. When more than one OMEGA is included in a compound of the present invention, the two or more OMEGAs may be the same or different. For embodiments of the invention that contain pyridinium ring systems, OMEGA is preferably $R^5$, or $R^6$ or both. For embodiments of the invention that contain a 4-quinolinium ring system, OMEGA is preferably $R^4$ or $R^5$, or both. For embodiments of the invention that contain a 2-quinolinium ring system, OMEGA is preferably $R^5$, $R^{11}$ or both. For all embodiments of the invention, preferably $R^5$ is an OMEGA.

One embodiment of the invention contains exactly two non-hydrogen substituents on the second heterocyclic ring, one of which is an OMEGA. Typically, $R^5$ is an OMEGA. Preferably, $R^5$ is an OMEGA and the substituent adjacent to $R^5$ ($R^6$ for pyridiniums, $R^4$ for 4-quinoliniums, and $R^{11}$ for 2-quinoliniums) is a non-hydrogen substituent. In one embodiment the substituent adjacent to $R^5$ is halogen, —$OR^8$, —$SR^8$, $NR^8R^9$, or —$OSO_2R^{19}$, more preferably halogen. In another embodiment of the invention, $R^5$ is —$OR^8$, —$SR^8$, or —$NR^8R^9$, preferably —$NR^8R^9$. In yet another embodiment of the invention, the substituent adjacent to $R^5$ is an OMEGA. $R^8$ and $R^9$ are as defined previously.

Several important properties of the formula I nucleic acid stains are shown in Table 1. Additional formula I dyes and some of their properties are listed in Tables 2 and 3.

TABLE 1

| Dye | Ex/Em (nm) | | | | | Properties on DNA | | | RNA |
| | $DNA^1$ | $RNA^1$ | $G^{+2}$ | $G^{-2}$ | $K_m^3$ | $QY^4$ | $P.B.^5$ | $F.E.^6$ | $F.E.^6$ |
|---|---|---|---|---|---|---|---|---|---|
| 61 | 500/527 | 510/530 | 506/529 | 510/572 | 1.0E07 | 0.46 | 1.10 | 353 | 502 |
| 63 | 514/531 | 515/537 | 514/537 | 518/603 | 3.9E06 | 0.24 | 1.08 | 582 | 696 |
| 613 | 506/523 | 508/529 | 506/527 | 506/533 | 5.3E06 | 0.33 | 1.14 | 225 | 1614 |
| 619 | 488/517 | 492/529 | 488/521 | 480/525 | 9.7E06 | 0.62 | 0.89 | 301 | 518 |
| 624 | 480/501 | 485/505 | 478/530 | 489/529 | 5.0E06 | 0.58 | 1.17 | 661 | 1435 |
| 628 | 488/506 | 490/510 | 484/526 | 485/531 | 7.0E06 | 0.40 | 1.13 | 771 | 166 |
| 591 | 509/532 | 517/536 | 516/540 | 516/540 | 4.8E06 | 0.09 | 1.11 | 169 | 653 |
| 634 | 510/530 | 511/533 | 511/529 | 515/610 | 2.0E06 | 0.18 | 1.10 | 176 | 122 |
| 73 | 508/525 | 510/531 | 508/530 | 509/532 | 4.4E06 | 0.31 | 1.12 | 700 | 371 |
| 715 | 487/507 | 490/523 | 485/513 | 489/517 | 1.2E07 | 0.52 | 1.09 | 1330 | 107 |
| 744 | 512/529 | 513/535 | 513/532 | 516/606 | 2.7E06 | 0.17 | 1.11 | 264 | 132 |
| Thiazole Orange | 510/530 | 509/535 | 511/530 | 510/532 | 4.8E06 | 0.18 | 1.01 | 143 | 811 |

[1]Fluorescence spectra obtained using a standard ratio of 50 μM bp of DNA (bases of RNA) to 1 μM dye (standard solution) in Tris buffered saline (10 mM Tris base, 1 mM EDTA and 50 mM NaCl), pH 7.4, in a spectrophotometer (absorbance), or in a fluorometer (emission) using 10-fold less dye and nucleic acid.
[2]Intracellular spectra for dyes loaded at optimal cell densities and dye concentrations, obtained in water using a fluorometer, where $G^+$ is *Staphylococcus aureus* and $G^-$ is *Escherichia coli*.
[3]DNA affinity ($K_m$) determined by linear fitting of plots of reciprocal fluorescence enhancement versus reciprocal DNA concentration, as measured on a microtiter plate fluorescence reader (CytoFluor ™, Millipore).
[4]Quantum yield (QY) of dye on DNA (standard solution in Tris buffered saline, as above, adjusted to pH 10) in comparison with fluorescein, which is assumed to have a quantum yield of 0.92 under the test conditions.
[5]Photobleaching (P.B.), expressed as the residual fluorescence from the new dye relative to that of fluorescein under identical conditions. A 0.05 OD standard solution in Tris buffered saline (as above) is illuminated at 485 nm (ex. bandwidth of 20 nm) and fluorescence is measured at time 0 and 30 min. Fraction of new dye fluorescence after 30 minutes is divided by fraction of fluorescein fluorescence remaining under identical conditions.
[6]Fluorescence enhancement (F.E.) is the fluorescence of the standard solution (as above) divided by the fluorescence of the same dye in the absence of nucleic acids (both measured in plastic cuvettes).

TABLE 2

| DYE | EX max/EM max | QY (DNA) | QY (RNA) | Kp |
|---|---|---|---|---|
| Thiazole Orange | 510/530 | 0.18 | 0.15 | 4.8 E6 |
| 61 | 500/527 | 0.46 | 0.34 | 1.0 E7 |

TABLE 2-continued

| DYE | EX max/EM max | QY (DNA) | QY (RNA) | Kp |
|---|---|---|---|---|
| 63 | 514/531 | 0.24 | | 3.9 E6 |
| 64 | 450/523 | | | |
| 71 | 508/526 | 0.31 | | |
| 72 | 515/535 | 0.026 | | 1.2 E6 |
| 73 | 508/525 | 0.31 | | 4.4 E6 |
| 200 | 739/759 | | | |
| 542 | 510/527 | | | |
| 578 | 470/504 | | | 4.1 E5 |
| 582 | 516/533 | | | |
| 591 | 509/532 | 0.09 | 0.13 | 4.8 E6 |
| 613 | 506/523 | 0.33 | | 5.3 E6 |
| 616 | 471/510 | | | 3.8 E5 |
| 619 | 488/517 | 0.62 | 0.22 | 9.7 E6 |
| 621 | 635/656 | | | |
| 624 | 480/501 | 0.58 | 0.57 | 5.0 E6 |
| 628 | 488/506 | 0.40 | | 7.0 E6 |
| 630 | 517/544 | 0.19 | | |
| 633 | 489/508 | 0.12 | | 7.4 E5 |
| 634 | 510/530 | 0.18 | | 2.0 E6 |
| 637 | 601/622 | 0.28 | | |
| 639 | 513/548 | 0.20 | | 8.0 E6 |
| 640 | 471/516 | | | |
| 641 | 503/526 | 0.35 | | 2.0 E7 |
| 672 | 586/611 | | | |
| 720 | 487/507 | 0.52 | | 1.2 E7 |
| 742 | 570/611 | | | |
| 752 | 494/518 | 0.51 | | |
| 758 | 504/524 | 0.44 | | 8.5 E6 |
| 760 | 483/510 | 0.68 | | |
| 764 | 486/508 | 0.58 | 0.46 | 1.1 E7 |
| 765 | 506/524 | 0.50 | | 1.1 E7 |
| 770 | 526/549 | | | 1.7 E6 |
| 774 | 517/533 | | | 7.9 E6 |
| 776 | | 0.65 | | |
| 780 (Cl) | 513/536 | 0.09 | | 3.4 E6 |
| 780 (S) | | 0.31 | | |
| 830 | 517/533 | | | |
| 834 | 486/507 | | | |
| 835 | 495/518 | | | |
| 853 | 516/555 | | | |
| 854 | 483/520 | | | |
| 856 | 502/523 | 0.43 | | |
| 5103 | 511/530 | 0.18 | | 5.4 E6 |
| 6104 | 505/523 | 0.52 | | 1.3 E7 |

TABLE 3

| DYE # | X | heterocycle | $R^1$ | $R^2$ | $R^4$ | $R^5$ | $R^{11}$ | $R^{12}$ | n |
|---|---|---|---|---|---|---|---|---|---|
| 125 | S | 2-pyridinium | H | Me | H | phenyl | — | — | 0 |
| 578 | S | 4-pyridinium | H | Me | Cl | phenyl | — | — | 0 |
| 616 | S | 4-pyridinium | H | Me | Cl | o-MeO-phenyl | — | — | 0 |
| 640 | S | 4-pyridinium | H | Me | H | phenyl | — | — | 0 |
| 742 | S | 4-pyridinium | H | Me | n-butyl | phenyl | — | — | 1 |
| 64 | S | 2-quinolinium | H | Me | H | phenyl | H | H | 0 |
| 61 | S | 4-quinolinium | H | Me | n-butyl | phenyl | H | H | 0 |
| 63 | S | 4-quinolinium | H | Me | H | phenyl | H | H | 0 |
| 71 | S | 4-quinolinium | H | Me | n-butyl | thienyl | H | H | 0 |
| 72 | S | 4-quinolinium | H | Me | H | Me | phenyl | H | 0 |
| 73 | S | 4-quinolinium | H | Me | H | cyclohexyl | H | H | 0 |
| 130 | S | 4-quinolinium | H | Me | —NH-phenyl | phenyl | H | H | 0 |
| 100 | S | 4-quinolinium | H | Me | n-butyl | phenyl | H | H | 2 |
| 200 | S | 4-quinolinium | H | Et | Cl | phenyl | H | H | 0 |
| 542 | S | 4-quinolinium | H | Me | H | cyclohexenyl | H | H | 0 |
| 582 | S | 4-quinolinium | H | Me | Cl | p-MeO-phenyl | H | H | 0 |
| 591 | S | 4-quinolinium | H | Me | Cl | phenyl | H | H | 0 |
| 613 | S | 4-quinolinium | H | Me | Me | phenyl | H | H | 0 |
| 619 | S | 4-quinolinium | H | Me | —NEt$_2$ | phenyl | H | H | 0 |
| 621 | S | 4-quinolinium | H | Me | n-butyl | phenyl | H | H | 1 |
| 624 | O | 4-quinolinium | H | Me | n-butyl | phenyl | H | H | 0 |
| 628 | S | 4-quinolinium | H | Me | —OMe | phenyl | H | H | 0 |
| 630 | S | 4-quinolinium | H | Me | phenyl | phenyl | H | H | 0 |
| 633 | O | 4-quinolinium | H | Me | Cl | phenyl | H | H | 0 |
| 634 | S | 4-quinolinium | H | Me | H | n-hexyl | H | H | 0 |
| 637 | O | 4-quinolinium | H | Me | n-butyl | phenyl | H | H | 1 |
| 639 | S | 4-quinolinium | H | Me | phenyl | Me | H | H | 0 |
| 641 | S | 4-quinolinium | H | Me | —SMe | phenyl | H | H | 0 |
| 672 | O | 4-quinolinium | H | Me | —OMe | phenyl | H | H | 1 |
| 720 | S | 4-quinolinium | H | Me | —OEt | phenyl | H | H | 0 |
| 752 | S | 4-quinolinium | H | Me | morpholinyl | Me | H | H | 0 |
| 758 | S | 4-quinolinium | Cl | Me | n-butyl | phenyl | H | H | 0 |
| 760 | S | 4-quinolinium | H | Me | —NEt$_2$ | phenyl | H | —OMe | 0 |
| 764 | S | 4-quinolinium | H | Me | —O-iPr | phenyl | H | H | 0 |
| 765 | S | 4-quinolinium | H | Me | cyclohexyl | phenyl | H | H | 0 |
| 770 | S | 4-quinolinium | —OMe | Me | H | phenyl | H | H | 0 |
| 774 | S | 4-quinolinium | H | Me | Br | phenyl | H | H | 0 |
| 776 | S | 4-quinolinium | H | Me | —N-nPr$_2$ | phenyl | H | H | 0 |
| 780 (Cl) | S | 4-quinolinium | H | Me | Cl | cyclohexyl | H | H | 0 |
| 780 (S) | S | 4-quinolinium | H | Me | —SMe | cyclohexyl | H | H | 0 |
| 830 | S | 4-quinolinium | H | Me | Cl | thienyl | H | H | 0 |
| 834 | S | 4-quinolinium | H | Me | F | phenyl | H | H | 0 |
| 835 | S | 4-quinolinium | H | Me | —O-phenyl | phenyl | H | H | 0 |
| 853 | S | 4-quinolinium | H | Me | —S-2-pyridyl | phenyl | H | H | 0 |
| 854 | S | 4-quinolinium | H | Me | —OSO$_2$CF$_3$ | phenyl | H | H | 0 |
| 856 | S | 4-quinolinium | H | Me | N—Me-piperazyl | phenyl | H | H | 0 |

TABLE 3-continued

| DYE # | X | heterocycle | $R^1$ | $R^2$ | $R^4$ | $R^5$ | $R^{11}$ | $R^{12}$ | n |
|---|---|---|---|---|---|---|---|---|---|
| 5103 | S | 4-quinolinium | H | Me | Cl | phenyl | H | —OMe | 0 |
| 6104 | S | 4-quinolinium | H | Me | cyclohexyl | Me | H | H | 0 |

Formula II Dyes

The dyes of formula II are lipophilic fluorescent dyes that give an enhanced fluorescence when complexed to intracellular nucleic acids. The dyes of formula II label only live Gram positive bacteria and label all dead bacteria, whether Gram positive or negative. The formula II dyes have a very low permeability to live Gram negative organisms. Preferred formula II dyes complexed with nucleic acids have an emission maximum of between about 580 nm and about 650 nm, resulting in an orange-red fluorescent signal in stained cells. In addition, formula II dyes typically have a higher binding affinity than formula I dyes and effectively compete for nucleic acid binding. In the presence of both dyes, live Gram positive organisms and all dead organisms typically stain according to the response characteristic of the formula II dye (e.g. orange-red). Even where the formula II dye does not completely displace the formula I dye, when used in combination, the fluorescent response of the live Gram positive organisms and dead organisms is nevertheless distinguishable from that of the live Gram negative organisms. If the sample is known to contain only Gram negative bacteria, the dye of formula II by itself will distinguish between viable and dead bacteria. Conversely, if the sample is known to contain only live bacteria, the dye of formula II will distinguish between Gram positive and Gram negative bacteria.

The fluorescent dyes of formula II have the structure:

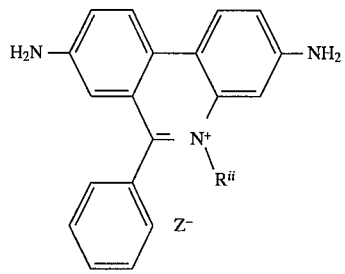

where $R^{ii}$ is $C_4$-$C_8$ alkyl. Preferably $R^{ii}$ is $C_6$-$C_8$ alkyl. Z is a biologically compatible counterion as described earlier. Although the dyes of formula II are similar in structure to ethidium bromide, they are permeant to cell membranes rather than impermeant. No loss of quantum yield is seen, e.g. butidium ($R^{ii}$=$C_4$) is 1.05× the quantum yield of ethidium bromide (or about 0.25) and hexidium ($R^{ii}$=$C_6$) is 1.10× the quantum yield of ethidium bromide (0.27) (quantum yields measured bound to calf-thymus DNA).

Formula III Dyes

Fluorescent formula III dyes are membrane impermeant dyes that give a fluorescent signal only in dead cells, i.e. cells with compromised plasma membrane integrity, whether Gram negative or Gram positive. The dyes of formula III have a much higher binding affinity for nucleic acids than the fluorescent dyes of either formula I or formula II and will therefore bind preferentially in the presence of the other two dyes. Generally, the complexed dye in bacteria has a broad emission spectrum between about 500 nm and about 650 nm, preferably with a peak emission at about 530 nm to about 590 nm, resulting in a yellow green fluorescent signal in stained cells, which is spectrally different from the preferred emission spectrum of either formula I or formula II dyes. Because the dyes of formula III only stain the intracellular nucleic acids of dead cells, the formula III dyes can be used without the combination of other dyes to determine the viability of cells. Any of the dyes described in patent applications DIMERS OF UNSYMMETRICAL CYANINE DYES (Ser. No. 07/761,177 filed Sep. 16, 1991 by Yue et al.) now abandoned, UNSYMMETRICAL CYANINE DYES WITH CATIONIC SIDE CHAIN (Set. No. 07/833,006 filed Feb. 8, 1992 by Yue, et al.) now U.S. Pat. No. 5,321,130, and DIMERS OF UNSYMMETRICAL CYANINE DYES CONTAINING PYRIDINIUM MOIETIES (filed Apr. 5, 1993 by Yue et al.) with the desired relative binding affinities and spectral characteristics may be used.

Formula III dyes can also be used in combination with other dyes to simultaneously determine both Gram reaction and viability, particularly where transmitted light observations are used. For example, in combination with a formula II dye, the live Gram positive cells will be stained by the formula II dye, the live Gram negative cells will be unstained, and the dead cells will be stained with the formula III dye.

Preferably the fluorescent dyes of formula III have the structure:

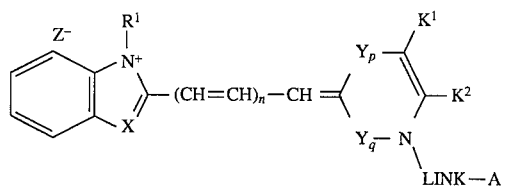

The heteroatom X is O, S, Se, or $C(CH_3)$. The nitrogen substituent $R^1$ is $C_1$-$C_6$ alkyl, preferably methyl. The methine bridge is either monomethine, trimethine or pentamethine, for n=0, 1 or 2. The aromatic ring component Y is —$CH_2$=$CH_2$—, with subscripts p and q equal to 0 or 1, such that p+q=1. Ring substituent $K^1$ and $K^2$ may be the same or different, and are independently hydrogen, an alkyl group having 1–6 carbons, or aryl; or $K^1$ and $K^2$ taken in combination complete a 6-membered aromatic ring to yield a quinolinium ring system.

LINK is an aliphatic chain containing a backbone of 4 to 19 methylene groups (—$CH_2$—), which is optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except that where A is H or CH₃ LINK must contain at least one N heteroatom. Preferred LINK chains contain two or three heteroatoms, each separated from one another by three methylenes. Preferably the heteroatom is N, where N is substituted by two alkyl groups of 1-6 carbons, which may be the same or different. Preferably LINK contains 12 or less methylene groups.

A is either H, CH₃ or is

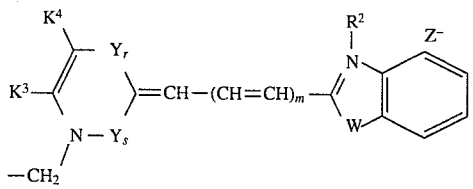

The heteroatom W is O, S, Se, or C(CH₃). The nitrogen substituent $R^2$ is $C_1$-$C_6$ alkyl, preferably methyl. The methine bridge is either monomethine, trimethine or pentamethine, for m=0, 1 or 2. The aromatic ring component Y is —CH₂=CH₂—, with subscripts r and s equal to 0 or 1, such that r+s=1. Ring substituent $K^3$ and $K^4$ may be the same or different, and are independently hydrogen, an alkyl group having 1-6 carbons, or aryl; or $K^3$ and $K^4$ taken in combination complete a 6-membered aromatic ring to yield a quinolinium ring system.

Fluorescent IV Dyes

Fluorescent IV dyes are fluorescent reagents that preferentially bind to an exterior component of a bacterium. The dye is typically a protein specific for cell wall, cell envelope, or flagellum components, such as an antibody or a lectin. Depending on how much is known about the makeup of the bacteria population in the sample being tested, the dye IV reagent is optionally a fluorescent antibody specific for a particular species or serotype, or a pan-specific antibody for a range of external cell markers. Alternatively the dye IV reagent is a fluorescent derivative of a lectin that is specific for a cell surface components such as N-acetylglucosamine, e.g. wheat germ agglutinin or others described in U.S. Pat. No. 5,137,810 to Sizemore, et al. (1992) or in the catalog of LECTINS AND LECTIN CONJUGATES, EY Laboratories, (San Mateo, Calif.). Lectins that differentiate Gram positive and Gram negative cells by their surface morphology are also suitable.

The fluorescent IV dyes are not nucleic acid stains and only stain the outer surface of the Gram positive cells, whether they are live or dead. Like the nucleic acid stains described previously, however, the fluorescent dyes of formula IV preferably have spectral properties different from the fluorescent dyes of formulae I, II, and III. The bullseye staining pattern can be used to distinguish bacteria where the spectral properties of the nucleic acid stains used in the method are similar or the same. Preferably, the fluorescent IV dyes are fluorescent blue derivatives, formed by the covalent attachment of a fluorophore with an emission maximum between about 410 nm and about 480 nm, to a protein such as wheat germ agglutinin or other Gram-positive specific lectin. Since the dye IV binds only to the external surface of Gram positive organisms, Whether live or dead, the dye IV dye is used to affirmatively indicate the existence of Gram positive organisms in a mixed population of unknown bacteria. For example, a combination of formula I dyes that stain green and dye IV that contain a blue fluorophore will give a blue fluorescent ring around green Gram positive bacteria and a green fluorescent signal without the blue ring for Gram negative bacteria. When used in combination with dyes of formulae I, II, and III, the addition of the dye IV provides a positive indicator of dead Gram positive organisms, which would otherwise only stain with the formula III dye and thus be indistinguishable from dead Grain negative organisms.

In one embodiment of the invention, the fluorescent dye IV is a protein that is covalently bound to a blue fluorescent fluorophore that emits between about 410 nm and about 480 nm. Preferably the protein is a lectin specific for N-acetylglucosamine, more preferably the protein is wheat germ agglutinin. Preferably, the blue fluorescent fluorophore is a pyrene, coumarin, acridone, naphthalene, or anthracene; more preferably an aminomethyl coumarin ( for example AMCA) or a pyrenyloxy sulfonic acid (e.g. CASCADE BLUE™, Molecular Probes, Inc., Eugene, Oreg.). A number of suitable, commercially available chemically reactive fluorophores, including blue fluorescent fluorophores, that can be used to label proteins such as wheat germ agglutinin and other lectins are available from Molecular Probes, Inc. Information about the spectral properties of such fluorophores is also available so that a suitable fluorophore with the desired spectral properties can be selected to label the protein of choice.

Method of Use

To make an aqueous dye solution for use in the invention, one or more dyes are selected so that each dye in the aqueous dye solution will give a staining response to the bacteria in the sample that is different from the staining response to the bacteria of any other dye in the solution. A different staining response means that whereas one dye stains one set of bacteria, another dye stains a different set, including a subset or an intersecting set or an independent set of bacteria. Typically, each dye in the solution will give a spectral response to the bacteria that is different from the spectral response of the other dyes, although the different staining response includes differences in the staining pattern, e.g. the difference between the nucleic acid dyes and the surface label.

The aqueous dye solution is made by dissolving the dyes directly in water or a buffer or in an organic water-miscible solvent such as DMSO, DMF, methanol, or ethanol. Typically the dyes are dissolved in DMSO and then diluted with water or buffer or a dilute protein solution to give an aqueous dye solution where each dye is present at a concentration sufficient to give a detectable fluorescent signal when combined with bacteria. The optimal concentration of dye in the aqueous solution depends on the type and amount of bacteria in the sample, the type of sample, as well as the dye itself. The optimal concentration results in the optimum fluorescent brightness per organism in the sample. Typically the concentration is between about 0.01 μM and about 100 μM, preferably from about 1 μM to about 30 μM. Generally the dyes are present in the staining solution within about a five-fold molar range, but the molar ratio one to the other of any particular combination of dyes in the sample can vary from about 1:1 to about 1:100, and may vary depending on whether the dyes are added to the sample of bacteria simultaneously or sequentially.

Non-specific binding by the dyes (e.g. binding to glass, extraneous fibers, or other non-bacterial debris) is diminished by the use of additives to the dye solution such as a dilute protein solution, particularly albumins. To prevent non-specific binding and give improved fluorescence response, particularly for solutions containing a dye of formula IV, the dye solution contains less than about 10% protein, preferably less that 5% protein, such as albumins. We have determined that less than 1.5% bovine serum albumin (BSA), and even as little as 0.001% BSA, has been found to be effective in improving the fluorescence of wheat-germ agglutinin conjugated to AMCA, resulting in a strong fluorescence signal that differentiates Gram positive from unbound dye and Gram negative bacteria without a wash step. Optionally, washing and resuspension are used to further improve the fluorescent response by eliminating background fluorescence.

The optional concentration of dye is generally determined according to the bacterial cell density. Bacterial cell density is determined from a series of absorption readings taken from a serial dilution of a suspension of cells compared with a duplicate plating of cells on an appropriate solid growth medium. The serial dilutions of plated cells are counted and compared with the absorption measurements of the same serial dilutions to determine the relationship between the number of cells or cell forming units per milliliter (cfu/mL) and absorption (cfu/mL/abs). Preferably the readings are taken at cell suspension concentrations between about $1 \times 10^3$ cfu/mL and about $1 \times 10^{10}$ cfu/mL, more preferably between about $1 \times 10^5$ cfu/mL and about $1 \times 10^9$ cfu/mL. Below about $10^3$ cfu/mL, absorption readings are not very reliable. A range of dye concentrations are then used to stain the bacteria suspensions at different cell densities to determine the optimal dye concentration for the cell density of the sample (Example 16). Typically, dye concentrations from about 1 mM down are tested. The tested ranges of cell density and dye concentration represent the ranges used for the invention. Table 4 summarizes the optimal staining conditions in terms of cell density and dye concentration for representative dyes of formula I.

nucleic acid binding affinity, and quantum yield contribute to the overall fluorescence of nucleic acid stains in microorganisms. Table 3 compares the relative fluorescence per cell for a number of different organisms using a variety of dyes of formula I.

TABLE 4

Optimal Staining Conditions*
Organism Density (cfu/mL)/Dye Concentration (μM)

| Sample[1] | Dye | | | | | | | | |
|---|---|---|---|---|---|---|---|---|---|
| | 61 | 63 | 613 | 619 | 624 | 628 | 591 | 634 | T.O. |
| B. cereus | 7.5E07/10 | 7.5E05/1.1 | 7.5E06/3.3 | 7.5E06/3.3 | 7.5E06/3.3 | 7.5E05/3.3 | 7.5E06/3.3 | 7.5E05/1.1 | 7.5E06/3.3 |
| M. luteus | 2.1E07/1.1 | 2.1E07/1.1 | 2.1E07/1.1 | 2.1E07/3.3 | 2.1E07/1.1 | 2.1E07/1.1 | 2.1E06/1.1 | 2.1E06/1.1 | 2.1E08/3.3 |
| S. pyogenes | 2.7E10/1.1 | 2.7E11/3.3 | 2.7E11/3.3 | 2.7E11/10 | 2.7E11/3.3 | 2.7E11/3.3 | 2.7E11/3.3 | 2.7E09/1.1 | 2.7E11/3.3 |
| S. aureus | 8.8E07/1.1 | 8.8E07/3.3 | 8.8E07/1.1 | 8.8E07/1.1 | 8.8E07/3.3 | 8.8E07/3.3 | 8.8E07/3.3 | 8.8E06/1.1 | 8.8E08/3.3 |
| C. sporogenes | 2.5E06/10 | 2.5E05/3.3 | 2.5E05/3.3 | 2.5E06/10 | 2.5E05/3.3 | 2.53E6/10 | 2.5E06/3.3 | 2.5E04/1.1 | 2.5E05/1.1 |
| E. coli | 2.9E07/10 | 2.9E07/10 | 2.9E08/10 | 2.9E07/10 | 2.9E07/10 | 2.9E07/10 | 2.9E08/10 | 2.9E07/10 | 2.9E08/10 |
| S. oranienburg | 2.3E07/10 | 2.3E07/10 | 2.3E07/10 | 2.3E08/30 | 2.3E08/10 | 2.3E08/10 | 2.3E08/10 | 2.3E07/10 | 2.3E08/10 |
| K. pneumonia | 2.3E08/3.3 | 2.3E07/10 | 2.3E09/10 | 2.3E08/30 | 2.3E09/30 | 2.3E09/10 | 2.3E09/30 | 2.3E07/1.1 | 2.3E08/10 |
| S. sonnei | 3.2E07/3.3 | 3.2E07/10 | 3.2E07/10 | 3.2E07/10 | 3.2E07/30 | 3.2E08/10 | 3.2E07/10 | 3.2E07/10 | 3.2E08/10 |
| P. aeruginosa | 5.8E07/3.3 | 5.8E08/3.3 | 5.8E09/10 | 5.8E09/30 | 5.9E07/3.3 | 5.8E08/3.3 | 5.8E07/10 | 5.8E07/1.1 | 5.8E09/10 |

[1]Bacillus cereus, Micrococcus luteus, Streptococcus pyogenes, Staphylococcus aureus, Clostridium sporogenes, Escherichia coli, Salmonella oranienburg, Klebsiella pneumonia, Shigella sonnei, Pseudomonas aeruginosa.

Factors such as degree of fluorescence enhancement with nucleic acid binding, self quenching, molar extinction coefficient, membrane permeability, intracellular partitioning,

TABLE 5

| | Fluorescence/Cell (ex 485/em 530)[1] | | | | | | | | |
|---|---|---|---|---|---|---|---|---|---|
| | Dye[2] | | | | | | | | |
| Sample[3] | 61 | 63 | 613 | 619 | 624 | 628 | 591 | 634 | Thiazole Orange |
| B. cereus | 196 | 93 | 242 | 827 | 709 | 613 | 58 | 154 | 51 |
| M. luteus | 49 | 33 | 75 | 149 | 162 | 149 | 375 | 58 | 21 |
| S. pyogenes | 0.01 | 0.01 | 0.02 | 0.06 | 0.05 | 0.04 | <0.01 | 0.03 | <0.01 |
| S. aureus | 15 | 5 | 10 | 47 | 44 | 34 | 3 | 15 | 3.2 |
| E. coli | 10 | 6 | 12 | 26 | 24 | 28 | 2 | 4 | 2 |
| S. oranienburg | 10 | 4 | 10 | 18 | 15 | 19 | 2 | 5 | 1 |
| K. pneumonia | 10 | 5 | 10 | 12 | 17 | 20 | 2 | 4 | 3 |
| S. sonnei | 6 | 3 | 6 | 13 | 11 | 16 | 1 | 4 | 1 |
| P. aeruginosa | 5 | 3 | 6 | 16 | 14 | 14 | 1 | 3 | 2 |

[1]Measured in a fluorescence microtiter plate reader with excitation and emission filters at 485 +/− 10 and 530 +/− 12, respectively. Fluorescence data are corrected for cell number; but are not corrected for cell volume or nucleic acid content.
[2]Optimal dye concentrations determined as in Table 4/Example 16.
[3]Suspension concentrations as used for Table 4/Example 16.

Enhanced cell fluorescence obtained with the formula I dyes is related to unexpected properties other than quantum yield alone. Table 6 compares the contribution of quantum yield to the overall enhancement of the fluorescence of bacteria stained with different formula I stains. The relative quantum yield and measured fluorescence of bacteria loaded with approximately optimal concentrations of each of eight representative formula I dyes and thiazole orange are compared. Quantum yield is determined as described above. Normalized quantum yield is determined to illustrate the fold-change in quantum yield of the formula I dyes compared with thiazole orange. The normalized fluorescence values represent the quantum yield of each dye divided by the quantum yield of thiazole orange. Fluorescence per cell is also scaled to thiazole orange values for both $E.\ coli$ and $S.\ aureus$ to allow direct comparison between relative (normalized) quantum yield and relative (normalized) fluorescence/cell.

TABLE 6

| | | | Normalized Fluorescence/cell (ex 485 nm/em 530 nm) | |
|---|---|---|---|---|
| Dye | QY | Normalized QY | Escherichia coli | Staphylococcus aureus |
| Thiazole Orange | 0.18 | 1.0 | 1 | 1.0 |
| 61 | 0.46 | 2.5 | 5 | 4.7 |
| 63 | 0.24 | 1.3 | 3 | 1.6 |
| 613 | 0.33 | 1.8 | 6 | 3.1 |
| 619 | 0.62 | 3.4 | 13 | 14.7 |
| 624 | 0.58 | 3.2 | 12 | 13.8 |
| 628 | 0.40 | 2.2 | 14 | 10.6 |
| 591 | 0.09 | 0.5 | 1 | 0.9 |
| 634 | 0.18 | 1.0 | 2 | 4.7 |

After the aqueous dye solution (preferably an aqueous solution of an optimized dye concentration) is combined with a bacteria sample, sufficient time is allowed for each dye in the solution to combine with bacteria in the sample before the resulting mixture of stained bacteria is prepared for illumination and observation. Generally, greater than about 10 minutes is sufficient time for the dye(s) to combine with the bacteria in the sample. Preferably the dye solution is combined with the sample between about 1 minute and about 30 minutes. For preferred dyes and dye combinations, the dye(s) combine with the sample in less than 5 minutes.

Figure 2:
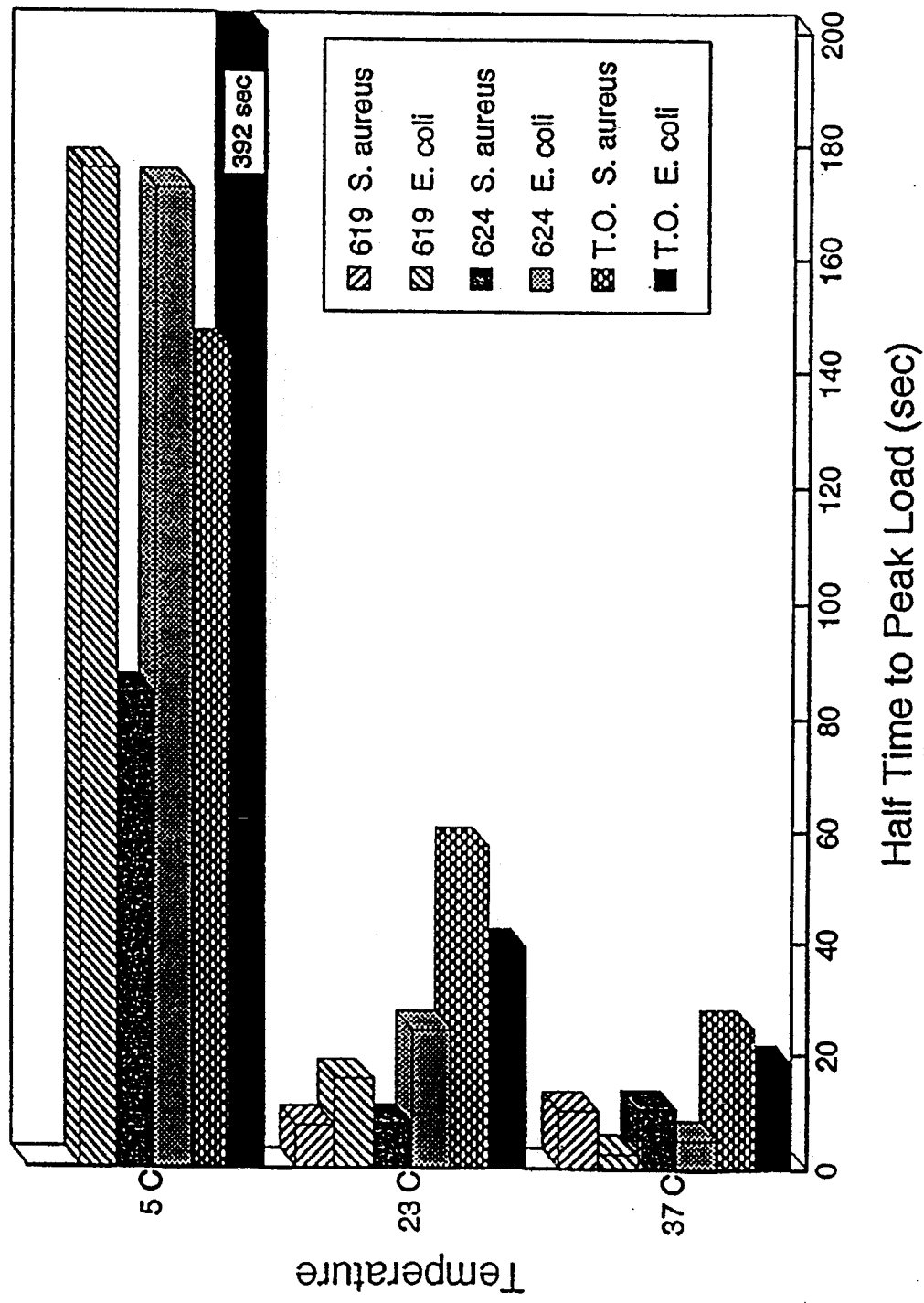
FIG. 2: Comparison of Loading Times for Formula I Dyes vs. Thiazole Orange (Example 15)

The loading time for formula I dyes in bacteria is depicted in Table 7 and FIG. 2 for a representative Gram positive species (S. aureus) and a Gram negative species (E. coli).

The loading time is expressed in two ways: as time required to reach half of the maximal fluorescence ($T_{0.5}$) and as the time required to reach 95% of the fluorescence measured at equilibrium ($T_{0.95}$) (see Example 15). Temperature affects a number of different mechanisms that influence cell loading times (see FIG. 2, Example 15). Preferably, the dye solution is combined with the sample at a temperature optimal for growth of bacteria in the sample within the operating parameters of the dyes, which fall between about 5° C. and about 50° C. Typically, the bacterial optimal growth temperature is about room temperature (23° C.).

TABLE 7

| | Loading Time (sec) | | | |
|---|---|---|---|---|
| | To peak | | To Equilibrium | |
| Dye | S. aureus $T_{0.5}$ | E. coli $T_{0.5}$ | S. aureus $T_{0.95}$ | E. coli $T_{0.95}$ |
| 61 | 3.4 | 18.2 | 66.9 | 270.9 |
| 63 | 7.9 | ND | 172.2 | ND |
| 613 | 9.1 | 11.3 | 149.0 | 163.1 |
| 619 | 7.3 | 15.5 | 34.3 | 243.3 |
| 624 | 7.6 | 24.3 | 27.6 | 89.4 |
| 628 | 19.6 | 36.8 | 47.2 | 89.9 |
| 591 | 6.3 | 25.3 | 116.3 | 73.3 |
| 634 | 14.5 | 12.5 | 86.3 | 154.2 |
| 73 | 10.0 | 23.3 | 145.1 | 58.6 |
| 715 | 6.8 | 21.6 | 216.4 | 221.6 |
| 744 | 12.2 | 22.9 | 81.5 | 249.7 |
| Thiazole Orange | 57.2 | 39.2 | 242.0 | 125.9 |

The dyed bacteria mixture is prepared for observation by any number of methods known in the art, including placing on microscope slides or in specialized containers for instrument measurements, with or without washing or resuspending cells. An outline of the many methods useful in preparing the bacteria cells for observation is found in the flow chart of FIG. 1. Preferably the cells are washed prior to illumination and observation to remove background fluorescence due to growth media or soluble extracellular materials, but washing is not essential.

Following preparation of the dyed bacteria mixture, the mixture is illuminated at a suitable absorption wavelength.

A suitable wavelength is one that comes within the range of absorption wavelengths for each of the fluorescent dyes being used. Typically, the mixture is illuminated by a light source capable of producing light at or near the wavelength of maximum absorption of the dye or dyes, such as by ultraviolet or visible lamp, an arc lamp, a laser, or even sunlight. Preferably the mixture is illuminated at one absorption wavelength shared by all the dyes in the aqueous dye solution, where the absorption wavelength is one that will give the brightest fluorescent signal for each of the dyes being used. Where the aqueous dye solution contains dyes of formula I, II, III, and dye IV the mixture is preferably illuminated between about 470 nm and 490 nm or between about 300 nm and about 365 nm.

Illumination of the dyed bacteria mixture at a suitable wavelength results in one or more illuminated bacteria that are then analyzed according to their fluorescent response to the illumination. The illuminated bacteria are observed with any of a number of means for detecting a fluorescent response emitted from the illuminated bacteria, including but not limited to visual inspection, cameras and film or other imaging equipment, or use of instrumentation such as fluorometers, plate readers, laser scanners, microscopes, or flow cytometers, or by means for amplifying the signal such as a photomultiplier.

The Gram reaction and optionally the viability of the bacteria in the test sample are then determined based on the fluorescent response that results from illumination. Table 8 summarizes the spectral response of representative dyes, where the dye representative of formula I has an emission maximum between about 500 nm and about 535 nm; the dye representative of formula II has an emission maximum between about 580 nm and about 650 nm, the dye is representative of formula III has an emission maximum between about 530 nm to about 590 nm, and the dye representative of dye IV has an emission maximum between about 410 nm and about 480 nm. As indicated in the table, each of the dyes reacts differently with bacteria depending on whether or not the bacteria are viable and whether the bacteria are Gram positive or Gram negative. Careful matching of other fluorescent stains with equivalent selective permeability, excitation/emission spectra, and preferential binding affinity for nucleic acids allows substitution of the preferred combination of nucleic acid stains to discriminate between many different organisms, whether live or dead.

Typically the method of the invention is used to determine the Gram reaction and/or viability of single cells. If fluorescent dyes are used to detect all members of the population (i.e. no transmitted light observations are required), however, cell size may even be below the resolution limit of the light microscope. In addition, the determination of Gram reaction and/or viability can be used as a basis for sorting the bacteria for further experimentation. For example, all Gram negative cells are sorted, or dead Gram positive cells are sorted, or viable Gram negative cells are sorted. The cells can be sorted manually or using an automated technique such as by fluorescence activated cell sorting (FACS) according to the procedures known in the art such as in U.S. Pat. No. 4,665,024 to Mansour, et al. (1987) (incorporated by reference).

Pure or mixed cultures of bacteria may be stained with different combinations of the formula I-III and dye IV dyes (see Examples 17–19). Bacteria can be detected in different solid or liquid food products by fluorescence techniques (see Example 23 A&B). Indigenous and contaminating bacteria from marine, estuarine, or fresh water environments are detected and characterized by fluorescence microscopy (see Example 22). Similarly, filtration and fluorescence techniques are combined for the detection and analysis of bacteria in purified water supplies. A wide variety of Gram negative and Gram positive bacteria can be detected, such as bacteria selected from the group consisting of *Bacillus cereus, Bacillus subtilus, Clostridium sporogenes, Corynebacterium xerosis, Micrococcus lute us, Mycobacterium phlei, Propionibacterium freunderreichii, Staphylococcus aureus, Streptococcus pyogenes, Lactobacillus acidophilus, Cytophaga psychrophila, Enterobacter aerogenes, Escherichia coli, Flavobacterium meningosepticum, Klebsiella pneumonia, Neisseria subflava, Pseudomonas aeruginosa, Rhizobium trifolii, Salmonella oranienburg, Shigella sonnei, Vibrio parahaemolyticus* or combinations thereof, as well as bacterial species from genera previously mentioned.

SOURCES FOR FLUORESCENT DYES

Formula I Dyes

A useful synthetic route to the dyes of formula I can be described in three parts, following the natural breakdown in the description of the compounds. In general, the synthesis of these dyes requires three precursors: a benzazolium salt,

TABLE 8

Figure 3:
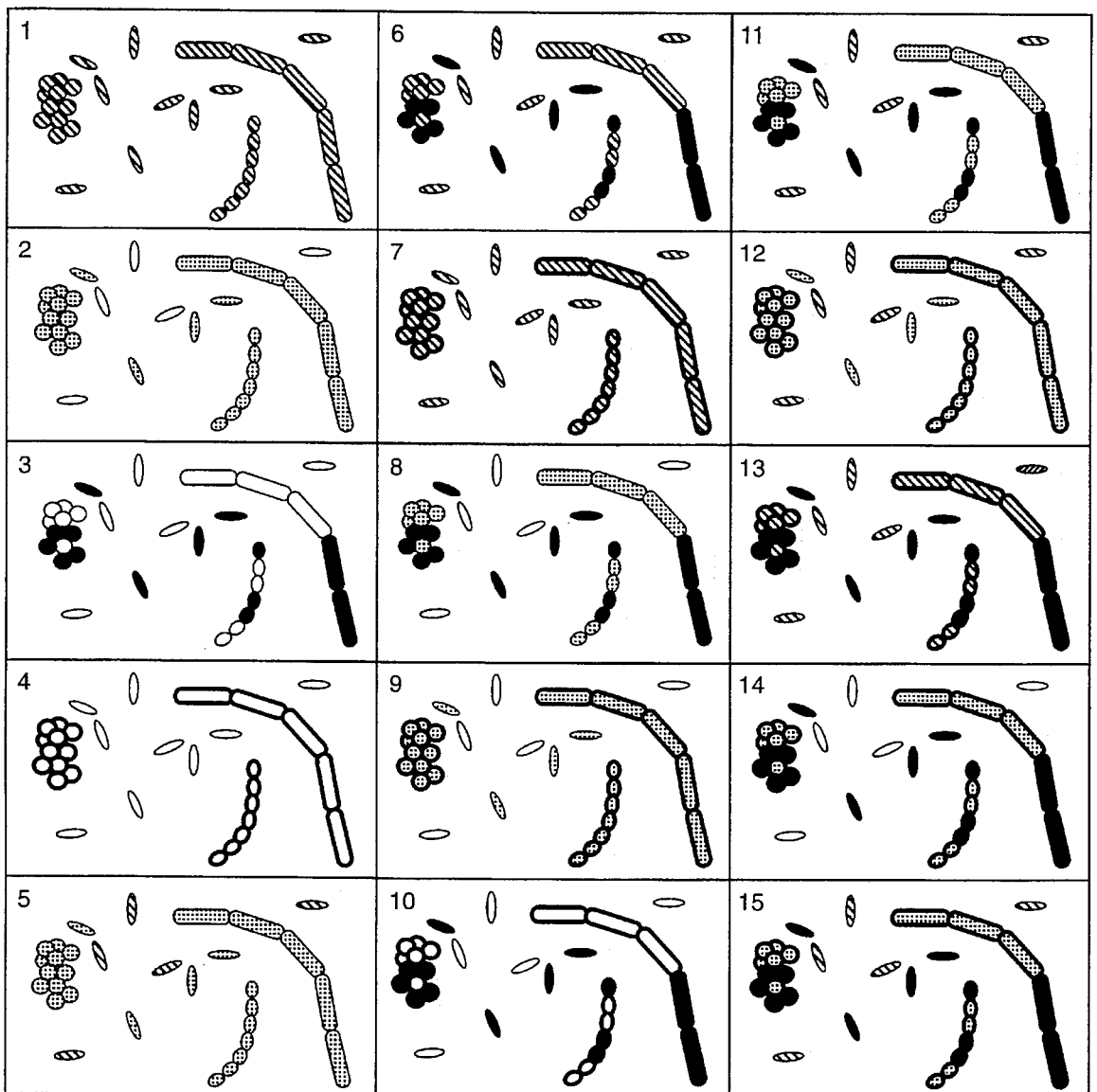
FIG. 3: Expected Staining Patterns Using Dyes Alone or in Combination. Each numbered panel (1–15) corresponds directly to the combination of stains shown in Table 6. The bottom panel is the key to the Gram sign and viability of several bacterial groups.

| Panel # in FIG. 3 | Dyes† | Live Gram (+) Bacteria | Live Gram (−) Bacteria | Dead Gram (+) Bacteria | Dead Gram (−) Bacteria |
|---|---|---|---|---|---|
| 1 | I | G | G | G | G |
| 2 | II | O | — | O | O |
| 3 | III | — | — | Y | Y |
| 4 | IV | B | — | B | — |
| 5 | I, II | O | G | O | O |
| 6 | I, III | G | G | Y | Y |
| 7 | I, IV | G with B | G | G with B | G |
| 8 | II, III | O | — | Y | Y |
| 9 | II, IV | O with B | — | O with B | O |
| 10 | III, IV | B | — | Y with B | Y |
| 11 | I, II, III | O | G | Y | Y |
| 12 | I, II, IV | O with B | G | O with B | O |
| 13 | I, III, IV | G with B | G | Y with B | Y |
| 14 | II, III, IV | O with B | — | Y with B | Y |
| 15 | I, II, III, IV | O with B | G | Y with B | Y |

Color Key: G = True-green  Y = Yellow-green  O = Orange  B = Blue Halo  — = Unstained a pyridinium (or quinolinium) salt (both of which have the appropriate chemical substituents), and (where n=1 or 2) a source for the methine spacer. Although the combination that enables these compounds to be useful stains for nucleic acids has not been described previously, the chemistry that is required to prepare and combine these precursors so as to yield any of the subject derivatives is generally well-understood by one skilled in the art. Although there are many possible variations that may yield an equivalent result, we provide herein some useful general methods for their synthesis and incorporation of chemical modifications.

The benzazolium moiety

A wide variety of derivatives of this type for use in preparing photographic dyes have been described, in particular by Brooker and his colleagues (Brooker, et al., J. AM. CHEM. SOC., 64, 199 (1942)). These synthetic precursors have the common structure:

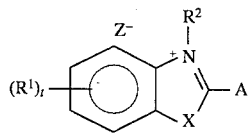

If X is O, the precursor compound is a benzoxazolium; if X is S it is a benzothiazolium; if X is Se it is a benzoselenazolium; if X is N or an alkyl substituted N it is a benzimidazolium; and if X is $CR^{16}R^{17}$ (where $R^{16}$ $R^{17}$, which may be the same or different, are independently alkyl groups having 1–6 carbons, or $R^{16}$ and $R^{17}$ taken in combination complete a five or six membered saturated ring) then it is an indolinium derivative. Commonly $R^{16}$ and $R^{17}$ are both methyl. However, methods for preparing compounds where $R^{16}$ and $R^{17}$ are not methyl are known (Hamer, "The Cyanine Dyes and Related Compounds", THE CHEMISTRY OF HETEROCYCLIC COMPOUNDS, Vol. 18, A. Weissberger, Ed., Interscience, New York (1964) (incorporated by reference)). The commercial availability of suitable starting materials and relative ease of synthesis make compounds with X=O or S the preferred intermediates.

$R^1$ is usually incorporated in the parent benzazole molecule prior to quaternization with an alkylating agent. $R^2$ is usually obtained by alkylation of the parent heterocycle with an alkylating agent $R^2$-Z where $R^2$ is an alkyl group having 1–6 carbons and Z is an electronegative group that frequently becomes the counterion on the resultant dye. $Z^-$ is a biologically compatible counterion that additionally is stable and synthetically accessible. The counterion may be exchanged for another counterion by methods known in the art, such as the use of ion exchange resins or by precipitation. Examples of $R^2$-Z include methyl iodide, diethyl sulfate, and hexyl-p-toluenesulfonate. Preferred $R^2$-Z are compounds that yield $R^2$=methyl, such as methyl iodide, methyl methanesulfonate, dimethyl sulfate, methyl trifluoromethanesulfonate or methyl p-toluenesulfonate.

A is a substituent whose nature is determined by the synthetic method utilized to couple the benzazolium precursor with the pyridinium or quinolinium precursor. When n=0, A is usually alkylthio, commonly methylthio, or A is chloro, bromo or iodo. When n=1 or 2, A is methyl. Only in the case of A=methyl is any part of A incorporated in the final compound.

The pyridinium or quinolinium moiety

The strongly conjugated ring system of the compounds of the present invention allows resonance stabilization of the single positive charge on the ring atoms to be distributed over the entire molecule. In particular, the charge is stabilized by partial localization on the heterocyclic nitrogen atoms of the dye. As the subject dye is drawn herein, the positive charge is formally localized on the benzazolium portion of the dye. However, it is commonly understood that a comparable resonance structure can be drawn in which the positive charge is formally localized on the pyridinium portion of the dye. Consequently we will usually refer to this portion of the molecule as a pyridine, pyridinium, quinoline or quinolinium moiety, although in the resonance structure shown it would formally be termed a dihydropyridine.

Compounds containing the quinolinium moiety in this invention differ from those that contain only the single pyridinium ring only in the presence of an additional aromatic ring containing four carbon atoms which is fused at the $R^6$ and $R^7$ positions of the parent structure. Consequently we will usually refer to this portion of the dye as the pyridine or pyridinium portion; however, except where reference is to a specific pyridine or pyridinium salt, it is understood that mention of pyridines or pyridinium salts encompasses benzopyridines and benzopyridinium salts, which are formally called quinolines or quinolinium salts. Mention of quinolines and quinolinium salts refer only to structures containing two fused aromatic rings.

In the synthesis of the dyes of the invention, the second heterocyclic precursor is usually a pyridinium salt that is already appropriately substituted. Less commonly, substituents can be incorporated into the pyridinium structure subsequent to attachment of the benzazolium portion of the dye. One of the substituents, which may be incorporated before or after incorporation of the pyridinium precursor, is an OMEGA.

Aside from the structural differences between pyridines and quinolines, there exist two major structural distinctions within the family of dyes described in the invention, related to the point of attachment of the pyridinium moiety. In one case (where m=0 and p=1) the position of attachment places the methine bridge adjacent to the heterocyclic atom (2-pyridines). In the more common case (where m=1 and p=0) the position of the nitrogen atom is separated from the position of attachment of the methine bridge by what is formally a carbon—carbon double bond $Y_M$ that completes the pyridinium ring (4-pyridines). In all cases m+p=1; that is, if m=1, p=0 and if m=0, p=1.

Typically the required pyridinium salt precursor has the structure

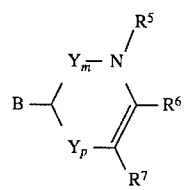

and the quinolinium salt precursor has the general structure

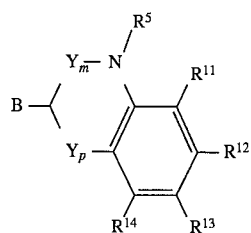

where the ring fragment Y is —CR$^3$=CR$^4$—, with subscripts p and m equal to 0 or 1, such that p+m=1. At all times, the ring is a 6 membered pyridinium-based heterocycle.

When n=0, B is methyl, or B is chloro, bromo or iodo. When n=1 or 2, B is methyl. Only when n=1 or n=2 is any part of B incorporated in the final compound.

There are several methods for the synthesis of the pyridinium portion of the dye. As the pyridinium structure contains the greatest possible variation in structure, as well as possible combinations of substituents, several routes to the pyridinium salt are possible, and in fact necessary.

The pyridinium and quinolinium precursors generally can be generated from the corresponding pyridine or quinoline by alkylation at nitrogen using a suitable alkylating agent R$^5$-Z. However, 2- and 4-pyridones and 2- and 4-quinolones are much more versatile chemical intermediates, with the added advantage of being easily prepared. For this reason, the preferred route to the pyridinium or quinolinium precursor will utilizes the corresponding pyridone or quinolone.

Useful methods for generation of the pyridone or quinolone intermediate include:
1) The condensation of an appropriately substituted aniline with diketene or its equivalent, followed by acid cyclization (HETEROCYCLIC COMPOUNDS, VOL. 4, R. C. Elderfield ed., John Wiley and Sons Inc., (1952) pp 1–331).
2) An Ullmann coupling between a 2- or 4-hydroxypyridone, or 2- or 4-hydroxyquinoline and an aryl halide. (Wawzonek et al., J. HETEROCYCLIC CHEM., 25, 381 (1988))

The resulting pyridone or quinolone can be further modified synthetically to create the desired pyridinium or quinolinium precursor by a variety of methods, dependent upon the location of the substituent OMEGA.

When R$^5$ is an OMEGA, the pyridone or quinolone can be treated with a powerful nucleophile such as a Grignard or an alkyl lithium reagent, to generate the pyridinium or quinolinium salt after acid-catalyzed dehydroxylation. Useful examples of strong nucleophiles include, but are not limited to, metal salts of alkanes such as butyl lithium, methyl lithium, phenyl lithium, or cyclohexyl magnesium chloride. For the case in which the desired 2- or 4-substituent is hydrogen, the pyridone or quinolone can be reduced with a reducing agent such as diisobutylaluminum hydride to the corresponding alcohol, which is then dehydroxylated.

The pyridone or quinolone can also be converted to a pyridinium or quinolinium salt by using a strong halogenating agent such as phosphorous oxychloride, phosphorous tribromide or diethylaminosulfur trifluoride. The resulting activated intermediate can be condensed with the appropriate benzazolium salt to form the dye directly. In the event that other substituents are desirable, the halopyridinium or haloquinolinium can be readily converted by using an appropriate reagent. For instance, treatment with alcohols or alkoxides yield alkoxy derivatives, treatment with thiols yield thioether derivatives, and treatment with amines yield amino derivatives. When the substituent at the 2 or 4 position is dialkylamino, the alkyl groups present on the dialkylamine can be the same or different, or when taken in combination may form a heteroalicyclic ring. For example, when the halopyridinium or haloquinolinium is treated with morpholine, the resulting substituent is a 6-membered heterocyclic ring containing nitrogen and oxygen atoms. This method can be used to attach a second OMEGA substituent as well, as when the halo-compound is treated with phenol to yield the phenoxide compound, or aniline to yield an anilino derivative.

When it is desired that the product dye have an R$^5$ substituent that is not an OMEGA, the desired OMEGA substituent can be introduced via the pyridone or quinolone intermediate as well. The 2- or 4-pyridone or 2- or 4-quinolone can be generated as above from treatment of the appropriate N-substituted aniline with diketene or its equivalent followed by acid catalyzed cyclization or by direct alkylation of the hydroxypyridone or hydroxyquinoline with an alkylating agent R$^5$-Z. The OMEGA substituent is then introduced by a strongly nucleophilic reagent, such as the magnesium or lithium salt of an OMEGA, to generate the corresponding alcohol, which is then dehydroxylated to the pyridinium or quinolinium salt in situ. For instance, treatment with phenyl lithium yields phenyl as an OMEGA in the 2- or 4-position. If the nucleophilic reagent is cyclohexyl magnesium chloride, the cyclohexyl is an OMEGA at the 2- or 4-position. For an OMEGA on other positions of the molecule, the appropriately substituted aniline can be convened to the pyridone or quinolone, which then undergoes further transformation to the pyridinium or quinolinium salt.

The methine bridge

The methine bridge consists of 1, 3 or 5 methine (—CH=) groups that bridge the benzazolium portion of the molecule and the pyridinium portion in such a way as to permit extensive electronic conjugation. The number of methine groups is determined by the specific synthetic reagents used in the synthesis.

When n=0, the synthesis of monomethine dyes commonly uses a combination of reagents where the methine carbon atom results from either A on the benzazolium salt or B on the pyridinium salt being methyl and the other of A or B being a reactive "leaving group" that is typically methylthio or chloro, but which can be any leaving group that provides sufficient reactivity to complete the reaction. This type of reaction to make unsymmetrical monomethine dyes from two quaternary salts was originally described by Brooker et al., supra. Whether A or B is methyl depends primarily on the relative ease of synthesis of the requisite precursor salts. Because the compounds in this invention typically contain the greatest variation on the pyridinium portion of the molecule; and furthermore, because 2-methyl and 4-methyl pyridines are usually easier to prepare than their corresponding methylthio analogs, we have usually chosen to prepare the subject monomethine dyes from precursors in which A=methylthio and B=methyl. Several descriptions of this type of reaction to prepare the subject dyes are given in the Examples. The condensing reagent in the case of monomethine dyes is typically a weak base such as triethylamine or diisopropylethylamine.

To synthesize trimethine dyes (n=1) both A and B are methyl. In this case the additional methine carbon is provided by a reagent such as N-methylformanilide or ethyl orthoformate (HOUBEN-WEYL, supra). Because under certain reaction conditions these same reagents can yield symmetrical cyanine dyes that incorporate two moles of a single quaternary salt, it is important to use the proper synthetic conditions, and a suitable ratio of the carbon-providing reactant to the first quaternary salt, that will promote formation of the proper intermediate. This intermediate is treated either before or after purification with the second quaternary salt to form the asymmetric cyanine dye. If desired, the counterion Z⁻ can be exchanged at this point. Although one can usually react either of the heteroaromatic precursor salts with the carbon-providing reagent to form the required intermediate, we have usually chosen to form the intermediate from the more readily available 2-methylbenzazolium salts as described by Brooker et al. A description of a method to synthesize a trimethine dye is given in Example 12.

Synthesis of the pentamethine dyes (n=2) uses the same precursors as used to prepare the trimethine dyes, and requires the same synthetic concerns about controlling the formation of an asymmetric intermediate. The three-carbon fragment that is required for the additional atoms in the bridge comes from a suitable precursor to malonaldehyde such as 1,1,3,3-tetramethoxypropane; 1,1,3-trimethoxypropene, 3-(N-methylanilino)propenal or other reagents. The condensing agent for this reaction is usually 1-anilino-3-phenylimino-1-propene (Sprague, supra).

Subsequent modification of dyes

As described earlier, the reactivity of the 2-halogenated pyridinium or quinolinium intermediate offers a variety of synthetic methods for attachment of various substituents at the 2-position. However, the reactivity of the 2-halo derivatives is preserved even after conjugation with the benzazolium precursor, enabling conversion of the resulting dye in which. $R^4$ is halogen into the appropriate alkoxy, amino and thiolate analogs, as described above for the pyridinium and quinolinium precursors. For example when 2-chloro-1-methyl-4-[2,3-dihydro-3 -methyl-(benzo-1,3-thiazol-2-yl)-methylidene]-quinolinium chloride is treated with morpholine, the corresponding 2-morpholine substituted derivative is obtained with an OMEGA being the morpholine ($R^4$= OMEGA=morpholinyl). In a similar manner, the 2-chloro substituted dye 591 can be transformed to dye 628 by simply stirring in methanol in the presence of a base such as triethylamine, to dye 619 with diethylamine or to dye 853 with 2-thiopyridine. Dyes can also be prepared by conversion of a 2-pyridone or 2-quinolone that has already been linked to the benzazolium moiety. For instance, 4-[2,3-dihydro-3-methyl-(benzo-1,3-thiazol-2-yl)-methylidene]-1-phenyl-1,2-dihydro-2-quinolone can be treated with phosphorous oxychloride and trifluoromethanesulfonate anhydride to generate dye 591 and dye 854 respectively.

Formula II Dyes

The dyes of formula II are synthesized according to modification of methods known in the art such as in Watkins, J. CHEM. SOC. 3059 (1952). In general, the substituent $R^{ii}$ is incorporated into the dye by reaction of a suitably amine-protected 3,8-diamino-6-phenylphenanthridine with an alkylating agent R-Z wherein Z is a "leaving group" that activates the alkyl portion of the reagent to nucleophilic displacement. Usually the protecting group is ethoxycarbonyl and R is the desired $R^{ii}$ substituent, i.e. and alkyl chain. Other amine-protecting groups such as carbobenzyloxy that prevent or reduce reaction of the alkylating reagent with the amines of the phenanthridine are also suitable. Typically, the leaving group Z from the alkylating agent provides the required counterion Z⁻ for the dye, which is a halogen (preferably iodide or bromide) or a sulfonate ester (preferably p-toluenesulfonate, p-chlorobenzenesulfonate or trifluoromethanesulfonate). Other counterions Z⁻ such as perchlorate, phosphate, sulfate, carbonate, bicarbonate, or tetrafluoroborate or anions of an organic carboxylic acid or sulfonic acid with less than about 8 carbons atoms are typically obtained by ion exchange subsequent to alkylation and deprotection.

Formula III Dyes

The dyes of formula III are commercially available from Molecular Probes, Inc. under the trademarks TOTO™, YOYO™, TO-PRO™, YO-PRO™, PO-PRO™, BO-PRO™, POPO™ and BOBO™ or can be synthesized from similar starting materials according to the procedures of patent applications DIMERS OF UNSYMMETRICAL CYANINE DYES (Ser. No. 07/761,177 filed Sep. 16, 1991 by Yue et al.), UNSYMMETRICAL CYANINE DYES WITH CATIONIC SIDE CHAIN (Ser. No. 07/833,006 filed Feb. 8, 1992 by Yue, et al.), and DIMERS OF UNSYMMETRICAL CYANINE DYES CONTAINING PYRIDINIUM MOIETIES (filed Apr. 5, 1993 by Yue et al.). The preparation of formula III dyes closely resembles the preparation of formula I dyes, as described above. Upon the preparation of an appropriately substituted cyanine dye, the compound is then dimerized, or a cationic side chain attached, as described in Examples 9–13, to generate the desired formula III dye.

Fluorescent IV Dyes

The fluorescent IV dyes are commercially available or synthesized by labeling a suitable protein or lectin with a reactive dye of the desired spectral properties, according to procedures known in the art, e.g. Brinkley, BIOCONJ. CHEM. vol.3, pp 1–13 (1992) (incorporated by reference), see also Example 16. Many such reactive dyes used for labeling or the labeled conjugates are commercially available from Molecular Probes, Inc.

The examples below are given so as to illustrate the practice of this invention. They are not intended to limit or define the entire scope of the invention.

Example 1

Preparation of 1,2-dihydro-4-methyl-1-phenyl-2-quinolone (1)

The following compound is prepared:

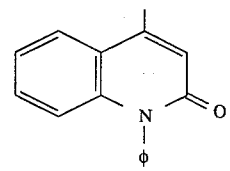

The starting 1,2-dihydro-4-methyl-1-phenyl-2-quinolone (1) is prepared either by an Ullmann coupling according to a literature procedure (e.g. S. Wawzonek and T. V. Truong, J. HETEROCYCLIC CHEM., 25, 381 (1988).) or via the reaction of the corresponding diarylamine with diketene followed by acid cyclization (e.g. R. C. Elderfield, ed., HETEROCYCLIC COMPOUNDS vol. 4, pp. 1–331, 1952). Thus 10.0 g (62.9 mmoles) of 2-hydroxy-4-methylquinoline is heated at reflux with 24.0 g (377 mmoles) of copper powder, 8.68 g (62.9 mmoles) of potassium carbonate and 19.2 g (94 mmoles) of iodobenzene for 48 hours. The reaction is cooled to room temperature, partitioned between water and ethyl acetate, filtered, and the organic layer is dried over magnesium sulfate. The crude product is purified on a silica gel column, eluting with 1:1 ethyl acetate/hexanes to yield 8.1 g of the desired product.

Example 2

Preparation of 2-chloro-4-[2,3-dihydro-3-methyl-(benzo-1,3-thiazol-2-yl)-methylidene]-1-phenylquinolinium iodide (dye 591)

The following compound is prepared:

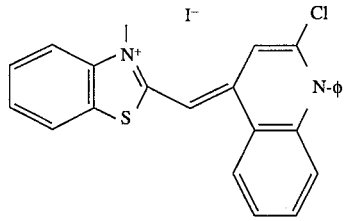

To 2.8 g (11.9 mmoles) of 1,2-dihydro-4-methyl-1-phenyl-2-quinolone (Example 1) in 20 mL of methylene chloride is added, 1.85 g of phosphorus oxychloride and a catalytic amount of dimethylformamide (Marson, TETRAHEDRON., 48, 3659 (1992)). The resulting mixture is heated to reflux for 24 hours. The reaction mixture is cooled to room temperature and 3.5 g (9.6 mmoles) of N-methyl-2-methylthiobenzothiazolium tosylate (Rye, et al., NUCLEIC ACIDS RES., 20, 2803 (1992)) is added followed by 1.3 mL (9.4 mmoles) of triethylamine. The mixture is stirred for an additional 6 hours. The crude product is purified on silica gel using ethyl acetate:chloroform:methanol, 3:3:1 as eluant. The product is then recrystallized from methanol/chloroform/ethyl acetate.

An additional synthetic route to this product utilizes 4-[2,3-dihydro-3-methyl-(benzo-1,3-thiazol-2-yl)-methylidene]-1,2-dihydro-1-phenyl-2-quinolone (4), which in turn is prepared from 1,2-dihydro-4-methyl-1-phenyl-2-quinolone (1) and 3-methyl-2-methylthiobenzothiazolium tosylate. Thus the lithium enolate of the (1) (prepared from treating the quinolone with 2.7 equivalent of lithium diisopropyl amide) or the silyl enolate (from (1) and trimethylsilyl trifluoromethanesulfonate and diisopropylethylamine) is stirred with the benzothiazolium tosylate. The desired intermediate (4) is isolated by column chromatography. The quinolone (4) is then treated with phosphorous oxychloride to generate the 2-chloro derivative.

Example 3

Preparation of 2-diethylamino-4-[2,3-dihydro-3-methyl-(benzo-1,3-thiazol-2-yl)-methylidene]-1-phenylquinolinium iodide (dye 619)

The following compound is prepared:

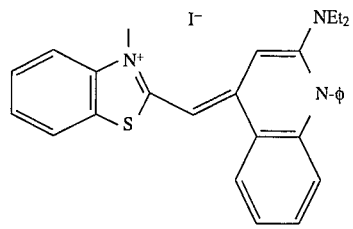

26 mg of 2-chloro-4-[2,3-dihydro-3-methyl-(benzo-1,3-thiazol-2-yl)-methylidene]-1-phenylquinolinium iodide (Example 2) is heated at 55° C. with 0.5 mL of diethylamine in 1.5 mL of DMF overnight. The desired product is isolated by a simple filtration.

Example 4

Preparation of 2-methoxy-4-[2,3-dihydro-3-methyl(benzo-1,3-thiazol-2-yl)-methylidene]-1-phenylquinolinium iodide (dye 628)

The following compound is prepared:

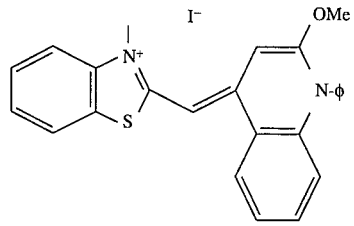

To 1.0 g (4.3 mmoles) of 1,2-dihydro-4-methyl-1-phenyl-2-quinolone (Example 1) in about 10 mL of methylene chloride, 2 mL of phosphorous oxychloride is added followed by a catalytic amount of dimethylformamide. After 3 hours under reflux, all the volatile components are removed under reduced pressure. Ten mL of methanol is added to the residue, and the solution is heated for an additional 2 hours. The methanol is removed under reduced pressure, and 10 mL of methylene chloride is added, followed by 1.56 g (4.3 mmoles) of N-methyl-2-methylthiobenzothiazolium tosylate and 1.5 mL of triethylamine (e.g. H. S Rye, et al., NUCLEIC ACIDS RES., 20, 2803 (1992)). The resulting mixture is stirred at room temperature for 3 days. The crude material is purified on a silica gel column by eluting with 5:5:1 ethyl acetate: chloroform: methanol.

The same dye is prepared by stirring dye 691 in methanol at room temperature in tile presence of 10 equivalents of triethylamine for about one hour.

Example 5

Preparation of 2-ethoxy-4-[3-methyl-2,3-dihydro(benzo-1,3-thiazolyl)-2-methylidene]-1-phenylquinolinium iodide (Dye 715)

The following compound is prepared:

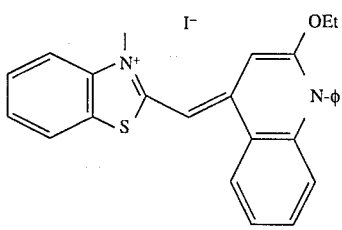

The compound is prepared as in Example 4 except that the volatile components are removed and replaced by 10 mL of ethanol instead of methanol and heated at 50° C. for 2 hours.

Example 6

Preparation of 2-butyl-4-[2,3-dihydro-3-methyl-(benzo-1,3-thiazol-2-yl)-methylidene]-1-phenylquinolinium iodide (dye 61)

The following compound is prepared:

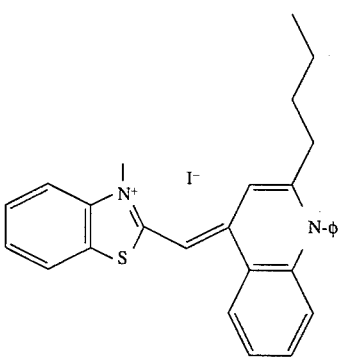

To 0.235 g (1 mmole) of 1,2-dihydro-4-methyl-1-phenyl-2-quinolone (Example 1) in 10 mL of THF at −78° C. under nitrogen, 1.2 equivalents of n-butyl lithium is introduced. The reaction is stirred at −78° C. for 15 minutes, and then the temperature is raised to 0° C. for another 30 minutes, at which time the reaction is quenched with acetic acid and all volatile components are removed under reduced pressure. The resulting residue is dissolved in 5 mL of methylene chloride and 0.367 (1 mmole) of the 4-methyl-2-methylthiobenzothiazolium tosylate is added followed by 0.28 mL (2 mmoles) of triethylamine. The reaction mixture is stirred for an additional 20 minutes at room temperature and the crude product is isolated as the iodide salt after a salt exchange. The crude iodide is recrystallized from methanol.

Example 7

Preparation of 2-butyl-4-[2,3-dihydro-3-methyl-(benzo-1,3-oxazol-2-yl)-methylidene]-1-phenylquinolinium iodide (dye 624)

The following compound is prepared:

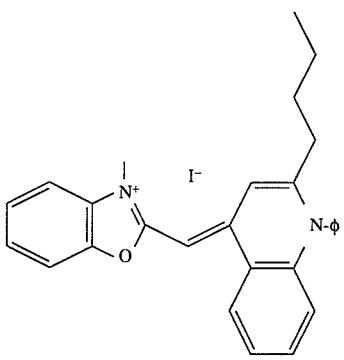

The procedure is the same as in Example 6 except that N-methyl-2-methylthiobenzoxazolium tosylate (e.g. H. S Rye, et al., NUCLEIC ACIDS RES., 20, 2803 (1992)) is used instead of the corresponding benzothiazolium tosylate.

Example 8

Preparation of 2-methyl-4-[2,3-dihydro-4-methyl-(benzo-1,3-thiazol-2-yl)-methylidine]-1-phenylquinolinium iodide (dye 613)

The procedure is analogous to that described in Example 6 except that methyl lithium is used instead of butyl lithium.

Example 9

Preparation of 4-[2,3-dihydro-4-methyl-(benzo-1,3-thiazol-2-yl)-methylidene]-1-phenylquinolinium (dye 63)

To 0.235 g of 1,2-dihydro-4-methyl-1-phenyl-2-quinoline (Example 1) in 10 mL of THF at −78° C., 0.4 mL of a 2.5 M DIBAL in cyclohexane is introduced via syringe and the mixture is stirred at low temperature for 30 minutes, and then at 0° C. for an additional 30 minutes. At the end of that period, 0.25 mL of acetic acid is added and all the volatile components are removed under reduced pressure. The residue is dissolved in 5 mL of methylene chloride and treated with 0.37 g of 3-methyl-2-methylthiobenzothiazolium tosylate in the presence of 1 mmole of triethylamine to yield the desired product.

Example 10 preparation of TOTO-1™

The following compound is prepared:

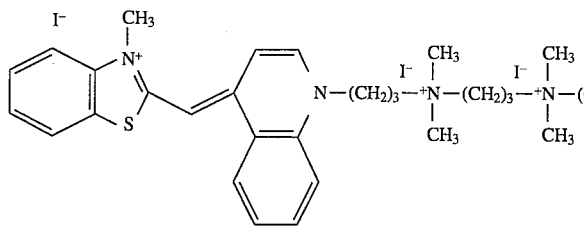

In the first step, 2-methylthiobenzothiazole (Aldrich Chemical Company, Milwaukee, Wis. is quaternized by heating at 120° C. with an equivalent of methyl p-toluenesulfonate (Compound 1A, also commercially available from TCI, Portland, Oreg.). N-(3-iodopropyl)-4-methylquinolinium iodide (Compound 1B) is prepared by heating lepidine (5.0 g, 35 mmol) with 100 g (340 mmol) of diiodopropane at about 100° C. for one hour. Ethyl acetate is added and filtered. Compounds 1A and 1B are condensed to yield 4-(3-methyl-2,3-dihydro-(benzothiazol)-2 -yliden-(4)-methyl)-1-(3'-iodopropyl)-quinolinium iodide (compound 1C) using methods known in the art [e.g. Brooker, et al., supra]. For instance when 12.0 g (27.3 mmol) of 1B is stirred with 10.0 g (27.2 mmol) of 1A in 200 mL of methylene chloride in the presence of 3.8 mL of triethylamine overnight at room temperature, 11.14 g of 1C is obtained by filtration. A mixture of 0.72 g of 1C is then dimerized by heating in a sealed tube with 69 mg of N,N,N',N'-tetramethylpropanediamine in 5 mL of DMF at 130° C. for one hour. After the reaction mixture cools down to room temperature, 40 mL of MeOH is added and stored at −20° C. overnight. The red solid is filtered and recrystallized from DMF/MeOH again to yield the pure product. TOTO-1 TM has a quantum yield of 0.34 bound to calf thymus DNA.

Example 11

Preparation of YOYO-1™

The following compound is prepared:

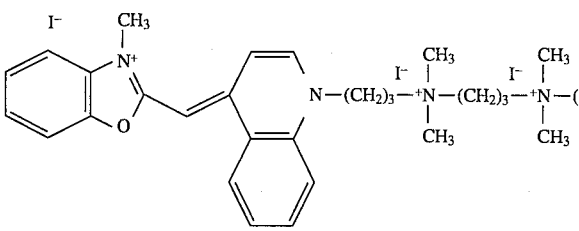

The starting material N-methyl-2-methylthiobenzoxazolium tosylate (2A) is prepared from the commercially available 2-mercaptobenzoxazole (Lancaster, Windham, N.H.). The 2-mercaptobenzoxazole (20 g, 132 mmol) is refluxed in 300 mL of acetone with 18.3 g (133 mmol) of potassium carbonate and 24 g (169 mmol) of methyl iodide for 2 hours to obtain 21 g of 2-methylthiobenzoxazole (2B) which then is heated with 24.5 g (132 mmol) of methyl tosylate at 160° C. for one hour to obtain 32.7 g of 2A. The benzoxazole dimer precursor, 4-(3 -methyl-2,3 -dihydro-(benzoxazol)-yliden-(4)-methyl)-1-(3'-iodopropyl)-quinolinium iodide (2C), is then prepared from 2A and 1B similar to above and is then dimerized by heating at about 90° C. with 0.5 equivalent of N,N,N',N'-tetramethylpropanediamine in DMF for 4 days. YOYO-1™ has a quantum yield of 0.52 bound to calf thymus DNA.

Example 12

Preparation of TO-PRO-1™

The following compound is prepared:

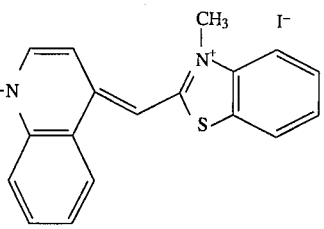

The target compound is obtained by heating 1C (1.0 g, 1.7 mmol) with 6 mL of a 25% trimethylamine in methanol in a sealed tube at 100° C. for four hours. The crude product is purified by recrystallizing from DMF and methylene chloride. TO-PRO*$^M$ has a quantum yield of 0.25 bound to calf thymus DNA.

Example 13

Preparation of YO-PRO™

The following compound is prepared:

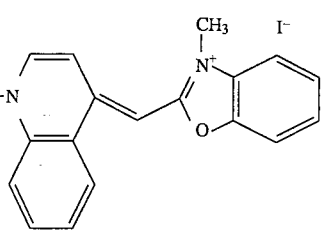

The compound is prepared in like manner as Example 12 (TO-PRO™) from 2C and trimethylamine and the crude product is recrystallized from DMF and methanol. YO-PRO™ has a quantum yield of 0.44 bound to calf thymus DNA.

Example 14

Optimization of Dye Loading

Determination of cell density

A culture of *E. coli* is washed by centrifugation and resuspended in water to its original volume. Using Corning 96-well microtiter plates with flat bottoms, 150 µL volumes of suspension are loaded per well. A single well of sterile water is the well background standard. Using a Dynatech MR600 microplate reader equipped with a 410 nm filter, absorbance is determined for the initial volumes of suspension. The suspension is diluted seven times by serial ten-fold dilutions in water, 150 µL of suspension per well, and the absorbance measured for each dilution. Following the absorbance measurements, each dilution loaded into wells is further diluted 1:10 and plated in duplicate on nutrient growth agar. The colonies are counted and expressed as colony forming units per milliliter (cfu/mL). Using the turbidity of the dilution in the microtiter plate, the suspension is diluted to a density of about $1\times10^9$ cfu/mL.

Optimization of Staining

The bacteria suspension, adjusted to a known density as described above, is diluted seven times by serial ten-fold dilutions in water; 150 µL of suspension per well. Three-fold serial dilutions of dye are used (30–0.04 µM); 50 µL of dye at 4× final concentration. Using Corning 96-well microtiter flat-bottom plates, a matrix is set up whereby the cell concentration decreases across the plate and the dye concentration decreases down the plate, final volume per well is 200 µL. The top row and first column are reserved for the control, sterile water. The plate is incubated at 37° C. for 30 minutes, then read in a Millipore Cytofluor™ 2300 96-well fluorescence microplate reader at a fixed excitation of 485+/−10 nm and each of three emission wavelengths, 530+/−12, 620+/−20, or 645+/−20 nm. The results determine the best dye range (30–1 µM) and the best cell concentrations (concentrated through first three ten-fold dilutions) for optimal dye loading. These results lead to the next staining optimization assay. Using the four dye dilutions and the four bacterial dilutions, many bacteria and dyes can be assayed quickly. The data collected allow the determination of optimal dye and cell concentration required for maximal fluorescence intensity per cell. Bacterial cell densities and dye concentrations that result in maximal fluorescence at defined emission wavelengths are shown in Table 2.

Example 15

Rate of Dye Loading

Relative rates of dye entry into bacteria

Half time ($T_{0.5}$) values for dye loading (Table 5) are obtained as follows: Either *E. coli* or *S. aureus* are grown in nutrient broth to log phase, washed by centrifugation, and resuspended in water to a density previously shown to allow dye loading to maximal fluorescence/cell (see Table 2). One centimeter pathlength acrylic cuvettes containing 3 mL of cell suspension are placed in a fluorescence spectrophotometer equipped with a temperature regulated cuvette holder and magnetic stirrer. The suspensions are brought to the appropriate temperature prior to dye addition. Millimolar dye stock solutions in DMSO are added at the appropriate concentrations to produce maximum attainable fluorescence/cell at the peak emission wavelength of each dye (see Table 2). The peak fluorescence excitation and emission wavelengths are determined by scanning the spectrum of each dye on similar suspensions of bacteria incubated for 30 min with the dye. Fluorescence intensity of the suspensions is measured at the peak excitation and emission wavelengths (as above) for the dye in each organism. Sampling of fluorescence is carried out at 5 or 10 Hz until the fluorescence signal appears to stabilize. Effect of temperature on dye loading:

The time required to load two different formula I dyes and thiazole orange into either *E. coli* or *S. aureus* at three different temperatures, 5° C., 23° C., and 37° C. (FIG. 2) is determined by equilibrating the bacterial suspensions at the appropriate temperatures and adding formula I stains as described above.

Example 16

Labeling protein with reactive dye

The following compound is prepared:

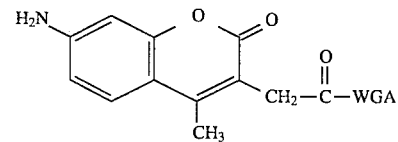

The AMCA labeled wheat germ agglutinin is prepared according to Brinkley, BIOCONJ. CHEM, 3, 1–13 (1992). The wheat germ agglutinin is dissolved at 5–10 mg/mL in 50–100 mM sodium bicarbonate buffer pH about 8.2 at room temperature. AMCA dye in a sufficient amount from a stock solution is added to contain 0.25 mg of succinimidyl ester for each 10 mg of wheat germ agglutinin. The solution of reactive AMCA dye should be added dropwise during a period of about 1 minute, using a Hamilton syringe (or equivalent) to the wheat germ agglutinin solution with stirring while in an ice bath. The solution is allowed to warm to room temperature and is stirred for exactly two hours. The conjugate is separated from the unreacted dye on a gel filtration column using an appropriate buffer and the degree of substitution of the conjugate is determined by the procedure described in Brinkley, BIOCONJ. CHEM,. 3, 1–13, (1992).

Example 17

Differentiation of Gram Reaction in a Mixed Bacterial Suspension with One Dye.

*Bacillus cereus* ($1\times10^6$/mL) and *Salmonella typhimurium* ($1\times10^7$/mL) are loaded with 5 µM of the formula II dye hexidium diluted into water. Bacteria are loaded for 15 minutes at room temperature. All bacteria are observed using a fluorescence microscope equipped with an excitation filter centered at about 480 nm, a 500 nm dichroic mirror and either a 510 nm long-pass filter or a bandpass filter centered at 590–610 nm. The microscope is coupled to a Photometrics Star-1 cooled CCD camera for quantitative digital imaging. Both organisms are detected by fluorescence and are distinguished morphologically. (Large brightly fluorescent G+ rods and slightly fluorescent G− rods).

Example 18

Differentiation of Mixed Bacterial Suspension with Two Dyes (I and II)

*Staphylococcus aureus* ($5 \times 10^5$/mL) and *Escherichia coli* ($1 \times 10^6$/mL) loaded in water with 2.5 μM of the formula I dye 628 and the formula II dye hexidium at 0.5 μM are detected using a flow cytometer equipped with a 488 nm argon laser. *E. coli* are counted by monitoring 510–530 nm fluorescence and *S. aureus* by monitoring fluorescence above 590 nm.

Example 19

Gram Reaction and Viability Determination of Pure Bacterial Culture with Three Dyes (I, II and III)

The Gram reaction and viability of the mixed bacterial suspension of Example 18 is determined by automated fluorescence microscopy by loading the bacteria with 1 μM of the formula III dye TOTO-1 in combination with 5 μM of the formula I dye 624 and 1 μM of the formula II dye hexidium. All dyes are prepared by dilution of 1 mM DMSO stock solutions in water. The triple staining eliminates the need for transmitted light observations or morphological discrimination. All dead bacteria appear very brightly fluorescent yellow-green, while live *S. aureus* bacteria appear orange-red and live *E. coli* appear green. Cell fragments that have no associated nucleic acids are not stained. Cells that are stained with a 2-fold lower concentration of the same formula I, II and III dyes are analyzed using a flow cytometer equipped with a 488 nm Argon laser. The cells are sorted or counted based on red/green ratio and spectral intensity. Three populations are discerned.

Example 20

Characterization of Bacteria from Purified Water Sample

Because of the very low numbers of organisms in many purified water systems it is necessary to concentrate the organisms prior to staining. This is accomplished by filtering a one liter volume of purified water through a blackened 13 mm diameter polycarbonate 0.22 μm pore Nucleopore membrane and either washing the organisms off of the filter into a small volume for subsequent staining, or by staining the organisms directly on the filter (FIG. 1). The complete four-stain protocol is most useful for this application. (FIG. 3, panel 15). Dye concentrations used under these conditions are kept low to achieve optimal staining i.e. 624 (1 μM), hexidium (1 μM), YOYO-1 (0.5 μM) and WGA-AMCA (5 μM).

Example 21

Loading Bacteria with Dyes in High and Low DMSO Concentrations

Different species of bacteria are loaded optimally with different formula I dyes at different concentrations. Since stock solutions of the stains are prepared in dimethylsulfoxide (DMSO) there may therefore be different concentrations of DMSO in the bacterial suspensions.

One mL of a suspension of *Salmonella typhimurium* grown in nutrient broth to a cell density of approximately $1 \times 10^9$ cfu/mL is washed by centrifugation at 10,000 rpm for 5 min in a microfuge and resuspended to $2.3 \times 10^8$ cfu/mL in water. 60 μL of a 0.5 mM solution of the formula I dye 624 in DMSO is added to 1 mL of cell suspension and the mixture is incubated at room temperature for 30 min (final DMSO concentration is 6%). The cell density is estimated by automated epifluorescence microscopy or flow cytometry using fluorescein optics. (G− rods, FIG. 3, panel 1).

One mL of a suspension of *Staphylococcus aureus* grown in nutrient broth to a cell density of approximately $1 \times 10^9$ cfu/mL is washed by centrifugation as above and resuspended to $8.8 \times 10^7$ cfu/mL in water. 5.5 μL of a 1 mM solution of the formula I dye 619 in DMSO is added to 5 mL of cell suspension and the mixture is incubated at room temperature for 30 min (final DMSO concentration is 0.11%). The cell density is estimated by automated epifluorescence microscopy or flow cytometry using fluorescein optics. (G+ cocci in clusters;, FIG. 3, panel 1).

Example 22

Characterization of Bacteria from Environmental Water Samples

Liter volumes of environmental water samples are filtered aseptically through sterile 13 mm blackened 0.22 μm pore polycarbonate filter membranes. Dye mixtures comprised of 3 μM of the formula I dye 624, 1 μM of the formula II dye hexidium, 0.5 μM of the formula III dye YOYO-1, and 5 μM of dye IV AMCA-WGA nucleic acid stains are prepared in water or in appropriate isotonic salt solutions. The combined dye solution is then passed through the membrane and allowed to incubate for 5–10 min at room temperature. The filter is then rinsed with a small volume of water or saline solution, removed from its holder, dried, mounted, and observed by epifluorescence microscopy. (FIG. 3, panel 15).

Example 23

Characterization of Bacteria from Food Samples

A. Surface

Bacteria are freed from the surface of solid samples, such as meat or vegetables, by vigorous agitation with sterile glass beads in an isotonic buffered saline solution. After settling of solid material and glass beads, the supernatant of bacteria and debris is removed and washed twice by centrifugation at 10,000 Xg for 10 min. The resulting pellet is resuspended in water containing 0.1% bovine serum albumin (BSA). The sample is stained with a dye mixture comprising 10 μM of the formula I dye 628, 2 μM of the formula II dye hexidium, 2 μM of the formula III dye TOTO-1, and 5 μM of dye IV AMCA-WGA nucleic acid stains in water plus BSA. The degree and nature of contamination is assessed by epifluorescence microscopy of the resulting mixture. (FIG. 3, panel 15) The suspension of bacteria freed from meat or vegetable surfaces using the glass bead technique is stained for 15 min at room temperature, then split into two portions, one of which is observed directly between a slide and coverslip using the fluorescence microscope, and the other concentrated onto a 13 nun blackened 0.22 μm pore polycarbonate filter membrane, washed once with isotonic saline and observed with the fluorescence microscope.

B. Suspension

A 1 mL sample of wine is concentrated by centrifugation at 10,000 rpm in a microfuge and washed twice in water containing 0.1% BSA. The resulting pellet is resuspended in water containing 0.1% BSA. The sample is stained with a dye mixture specified in pan A of Example 20 with 619 substituted for 628 as the formula I dye. The degree and nature of contamination is assessed by epifluorescence microscopy of the resulting mixture. Yeast are excluded because of their size.

The bioload of milk is determined by obtaining 1 mL samples of milk, which are washed by centrifugation as above. The pellet is then resuspended in 1 mL of sterile water and stained with the four-dye mixture (above) prior to filtration onto a 13 mm blackened 0.22 μm pore polycarbonate filter membrane. After washing with several 1 mL volumes of sterile water the filter membrane is mounted between a glass slide and coverslip and observed by epifluorescence microscopy (FIG. 3, panel 15).

It is to be understood that, while the foregoing invention has been described in detail by way of illustration and example, numerous modifications, substitutions, and alterations are possible without departing from the spirit and scope of the invention as described in the following claims.

What is claimed is:

1. A method of analyzing bacteria for Gram reaction, comprising:

a) combining a bacteria sample, simultaneously or sequentially, with an aqueous dye solution comprising a fluorescent dye of formula I, in combination with an aqueous dye solution comprising a fluorescent dye of formula II or an aqueous dye solution comprising a fluorescent dye IV or both, where each dye is present in solution in an amount sufficient to give a detectable fluorescent response and where each dye present in solution is selected such that its detectable fluorescent response, after staining and illumination of the sample, is different from the fluorescent response of any other dye being combined;

wherein said dye of formula I has the formula

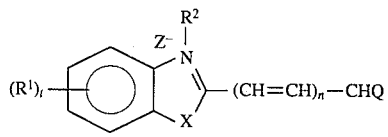

wherein each $R^1$ is independently H; or an alkyl group having from 1–6 carbons; or a trifluoromethyl; or a halogen; or $-OR^8$, $-SR^8$ or $-(NR^8R^9)$ where $R^8$ and $R^9$, which can be the same or different, are independently H; or alkyl groups having 1–6 carbons; or 1–2 alicyclic, heteroalicyclic, aromatic or heteroaromatic rings, containing 1–4 heteroatoms, wherein the hetero atoms are O, N or S: or $R^8$ and $R^9$ taken in combination are $-(CH_2)_2-L-(CH_2)_2-$ where L=a single bond, $-O-$, $-CH_2-$, or $-NR^{10}-$ where $R^{10}$ is H or an alkyl group having 1–6 carbons; and t=1–4;

$R^2$ is an alkyl group having 1–6 carbons;

X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons, or $R^{16}$ and $R^{17}$ taken in combination complete a five or six membered saturated ring:.

n=0, 1 or 2;

$Z^-$ is a biologically compatible counterion;

O has the formula Q1 or Q2

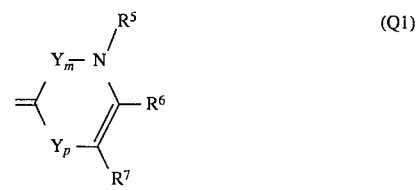

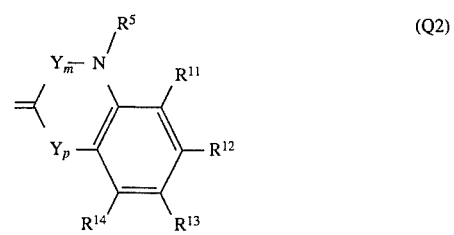

wherein

Y is $-CR^3=CR^4-$;

p and m=0 or 1, such that p+m=1;

$R^5$ is an alkyl, alkenyl, polyalkenyl, alkynyl or polyalkynyl group having 1–6 carbons; or $R^5$ is an OMEGA;

$R^3$, $R^4$, $R^6$ and $R^7$, which may be the same or different, are independently H; or an alkyl, alkenyl, polyalkenyl, alkynyl or polyalkynyl group having 1–6 carbons; or a halogen; or $-OH$, $-OR^8$, $-SR^8$, $-(NR^8R^9)$; or $-OSO_2R^{19}$ where $R^{19}$ is alkyl having 1–6 carbons, or perfluoroalkyl having 1–6 carbons, or aryl; or an OMEGA;

or $R^6$ and $R^7$, taken in combination are $-(CH_2)_v-$ where v=3 or 4, or $R^6$ and $R^7$ form a fused aromatic ring according to formula Q2;

$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or an OMEGA; or $-OH$, $-OR^8$, $-SR^8$, or $-(NR^8R^9)$;

OMEGA is a saturated or unsaturated, substituted or unsubstituted, cyclic substituent that has a total of 2–16 ring carbon atoms in 1–2 alicyclic, heteroalicyclic, aromatic, or heteroaromatic rings, containing 1–4 heteroatoms wherein the heteroatoms are O, N or S, that is unsubstituted or optionally substituted one or more times, independently, by halogen, alkyl, perfluoroalkyl, alkoxy or carboxyalkyl, having 1–6 carbons, and that is attached as $R^3$, $R^4$, $R^5$, $R^6$, $R^7$, $R^{11}$, $R^{12}$, $R^{13}$, or $R^{14}$ by a single O bond;

such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different;

said dye of formula II has the formula

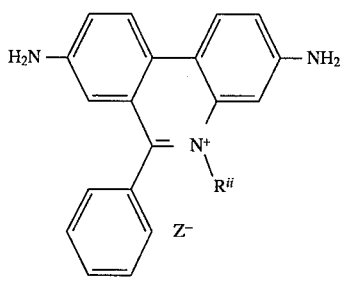

wherein $R^{ii}$ is a $C_4$–$C_8$ alkyl; and $Z^-$ is a biologically compatible counterion; and
said dye IV is a fluorescent reagent that preferentially binds to an exterior component of Gram-positive bacterium;

b) allowing sufficient time for each dye in solution to combine with one or more bacterium in the sample to give a dyed bacteria mixture;

c) illuminating the dyed bacteria mixture at a suitable absorption wavelength that results in one or more illuminated bacterium;

d) observing the illuminated bacterium with means for detecting the fluorescent response resulting from illumination; and e) analyzing the fluorescent response of said illuminated bacterium, wherein the fluorescent dye of formula I stains intracellular nucleic acids for all bacteria in the sample;

the fluorescent dye of formula II stains intracellular nucleic acids for all Gram positive bacteria in the sample; and
the fluorescent dye IV stains the external surface of all Gram positive bacteria in the sample.

2. A method as in claim 1 wherein said bacteria sample is combined with an aqueous dye solution comprising a fluorescent dye of formula I in combination with an aqueous dye solution comprising a fluorescent dye of formula II, where the fluorescent dye of formula I stains intracellular nucleic acids for all bacteria in the sample and the fluorescent dye of formula II stains intracellular nucleic acids for all Gram positive bacteria in the sample.

3. A method as in claim 1, where the fluorescent dye of formula I has the formula:

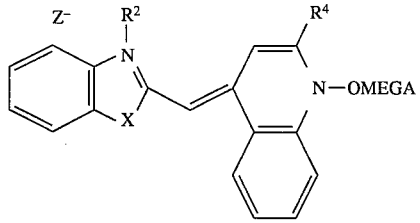

wherein
$R^2$ is methyl or ethyl;
X is O or S;
$R^4$ is H, alkyl, alkenyl, polyalkenyl, alkynyl or polyalkynyl having 1–6 carbons; or a halogen; or —$OR^8$, —$SR^8$, —$(NR^8R^9)$; or —$OSO_2R^{19}$;
OMEGA is phenyl or cyclohexyl; and
$Z^-$ is a biologically compatible ion;
and the fluorescent dye IV is a lectin that binds selectively to N-acetylglucosamine and is covalently bound to a fluorescent fluorophore.

4. A method, as claimed in claim 5, wherein for said dye of formula I, each $R^1$ is H, $R^2$ is ethyl or methyl, X=O or S, and n=0 or 1.

5. A method of analyzing bacteria for Gram reaction, comprising:

a) combining a bacteria sample, simultaneously or sequentially, with an aqueous dye solution comprising a fluorescent dye of formula II, in combination with an aqueous dye solution comprising a fluorescent dye of formula I or an aqueous dye solution comprising a fluorescent dye of formula III or an aqueous dye solution comprising a fluorescent dye IV or combinations thereof, where each dye is present in solution in an amount sufficient to give a detectable fluorescent response and where each dye present in solution is selected such that its detectable fluorescent response, after staining and illumination of the sample, is different from the fluorescent response of any other dye being combined;

wherein said dye of formula I has the formula

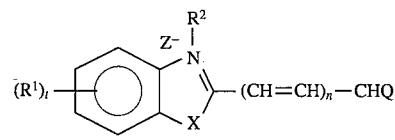

wherein
each $R^1$ is independently H; or an alkyl group having from 1–6 carbons; or a trifluoromethyl; or a halogen; or —$OR^8$, —$SR^8$ or —$(NR^8R^9)$ where $R^8$ and $R^9$, which can be the same or different, are independently H; or alkyl groups having 1–6 carbons; or 1–2 alicyclic, heteroalicyclic, aromatic or heteroaromatic rings, containing 1–4 heteroatoms, wherein the hetero atoms are O, N or S; or $R^8$ and $R^9$ taken in combination are —$(CH_2)_2$—L—$(CH_2)_2$— where L=a single bond, —O—, —$CH_2$—, or —$NR^{10}$— where $R^{10}$ is H or an alkyl group having 1–6 carbons; and t=1–4;

$R^2$ is an alkyl group having 1–6 carbons;

X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons, or $R^{16}$ and $R^{17}$ taken in combination complete a five or six membered saturated ring;

n=0, 1 or 2;

$Z^-$ is a biologically compatible counterion;

Q has the formula Q1 or Q2

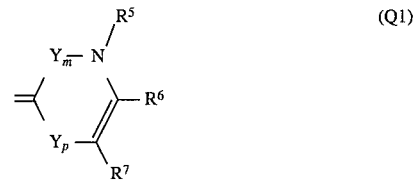 (Q1)

-continued

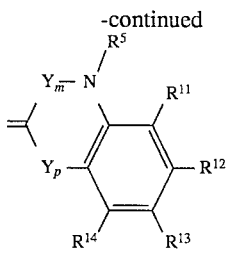
(Q2)

wherein

Y is —CR³=CR⁴—;

p and m=0 or 1, such that p+m=1;

R⁵ is an alkyl, alkenyl, polyalkenyl, alkynyl or polyalkynyl group having 1–6 carbons; or R⁵ is an OMEGA;

R³, R⁴, R⁶ and R⁷, which may be the same or different, are independently H; or an alkyl, alkenyl, polyalkenyl, alkynyl or polyalkynyl group having 1–6 carbons; or a halogen; or —OH, —OR⁸, —SR⁸, —(NR⁸R⁹); or —OSO₂R¹⁹ where R¹⁹ is alkyl having 1–6 carbons, or perfluoroalkyl having 1–6 carbons, or aryl; or an OMEGA;

or R⁶ and R⁷, taken in combination are —(CH₂)ᵥ— where v=3 or 4, or R⁶ and R⁷ form a fused aromatic ring according to formula Q2;

R¹¹, R¹², R¹³, and R¹⁴, which may be the same or different, are independently H; or an alkyl, alkenyl, polyalkenyl, alkynyl or polyalkynyl group having 1–6 carbons; or a halogen; or an OMEGA; or —OH, —OR⁸, —SR⁸, or —(NR⁸R⁹);

OMEGA is a saturated or unsaturated, substituted or unsubstituted, cyclic substituent that has a total of 2–16 ring carbon atoms in 1–2 alicyclic, heteroalicyclic, aromatic, or heteroaromatic rings, containing 1–4 heteroatoms wherein the hetero atoms are O, N or S, that is unsubstituted or optionally substituted one or more times, independently, by halogen, alkyl, perfluoroalkyl, alkoxy or carboxyalkyl, having 1–6 carbons, and that is attached as R³, R⁴, R⁵, R⁶, R⁷, R¹¹, R¹², R¹³, or R¹⁴ by a single bond;

such that at least one of R³, R⁴, R⁵, R⁶, R⁷, R¹¹, R¹², R¹³, and R¹⁴ is an OMEGA, and, where more than one of R³, R⁴, R⁵, R⁶, R⁷, R¹¹, R¹², R³, and R¹⁴ is an OMEGA, each OMEGA is optionally the same or different;

said dye of formula II has the formula

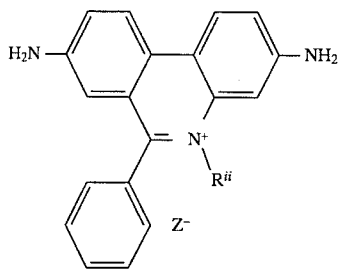

wherein R^{ii} is a C₄–C₈ alkyl; and Z⁻ is a biologically compatible counterion;

said dye of formula III has the formula

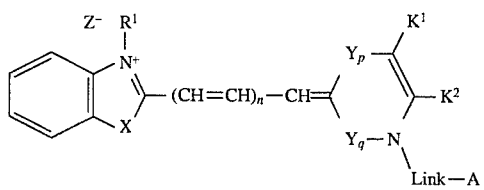

wherein

X is O, S, Se, or C(CH₃); and

R¹ is an alkyl group of 1–6 carbons;

n=0, 1 or 2;

Y is —CH₂=CH₂—;

p and q are equal to 0 or 1, such that p+q=1;

K¹ and K² may be the same or different, and are independently hydrogen, an alkyl group having 1–6 carbons, or aryl; or K¹ and K² taken in combination complete a 6-membered aromatic ring;

LINK is an aliphatic chain containing a backbone of 4 to 19 methylene groups (—CH₂—), optionally interspersed at one or more intervals with a heteroatom, each of which is independently N, O or S wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or CH₃, LINK must contain at least one N heteroatom;

A is H, CH₃ or is

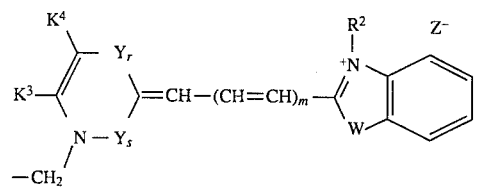

wherein

W is O, S, Se, or C(CH₃);

R² is an alkyl group of 1–6 carbons;

m=0, 1 or 2;

Y is —CH₂=CH₂—;

r and s equal to 0 or 1, such that r+s=1;

K³ and K⁴ may be the same or different, and are independently hydrogen, an alkyl group having 1–6 carbons, or aryl; or K³ and K⁴ taken in combination complete a 6-membered aromatic ring; and said dye IV is a fluorescent reagent that preferentially binds to an exterior component of Gram-positive bacterium;

b) allowing sufficient time for each dye in solution to combine with one or more bacterium in the sample to give a dyed bacteria mixture;

c) illuminating the dyed bacteria mixture at a suitable absorption wavelength that results in one or more illuminated bacterium;

d) observing the illuminated bacterium with means for detecting the fluorescent response resulting from illumination; and e) analyzing the fluorescent response of said illuminated bacterium, wherein the fluorescent dye of formula II stains intracellular nucleic acids for all Gram positive bacteria in the sample;

the fluorescent dye of formula I stains intracellular nucleic acids for all bacteria in the sample:.

the fluorescent dye of formula III stains the nucleic acids for all dead bacteria in the sample: and the fluorescent dye IV stains the external surface of all Gram positive bacteria in the sample.

6. A method as in claim 5 where each of the dyes present are present in concentrations between about 0.01 μM and about 100 μM.

7. A method as in claim 5 wherein the fluorescent dye of formula I has the formula:

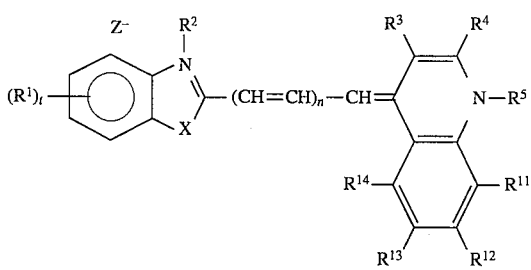

wherein

X is O or S; and at least one of $R^4$ and $R^5$ is an OMEGA.

8. A method as in claim 5 where the fluorescent dye of formula IV is a lectin that binds selectively to N-acetylglucosamine and is covalently bound to a blue fluorescent fluorophore that emits between 410 nm and 480 nm and the fluorophore is a pyrene, coumarin, acridone, naphthalene, or anthracene.

9. A method as in claim 5 wherein said bacteria sample is combined with an aqueous dye solution comprising a fluorescent dye of formula II in combination with an aqueous dye solution comprising a fluorescent dye of formula III, where the fluorescent dye of formula II stains intracellular nucleic acids for all Gram positive bacteria in the sample and the fluorescent dye of formula III stains intracellular nucleic acids for all dead bacteria.

10. A method as in claim 9 further comprising combining said sample with an aqueous dye solution comprising a fluorescent dye of formula I that stains intracellular nucleic acids for all bacteria in the sample.

11. A method as in claim 5, comprising: wherein step a) further comprises combining a bacteria sample, simultaneously or sequentially, with an aqueous dye solution comprising a fluorescent dye of formula II, in combination with an aqueous dye solution comprising a fluorescent dye of formula I or an aqueous dye solution comprising a fluorescent dye of formula III or an aqueous dye solution comprising a fluorescent dye IV or combinations thereof, where each dye present in solution is present in a concentration between about 1 μM and about 30 μM;

where the fluorescent dye of formula I has the formula:

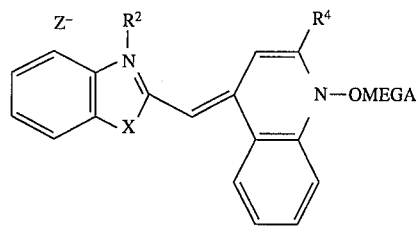

wherein $R^2$ is methyl or ethyl;

X is O or S;

$R^4$ is H, alkyl, alkenyl, polyalkenyl, alkynyl or polyalkynyl having 1–6 carbons; or a halogen; or —$OR^8$, —$SR^8$, —$(NR^8R^9)$; or —$OSO_2R^{19}$;

OMEGA is phenyl or cyclohexyl; and $Z^-$ is a biologically compatible ion;

where the fluorescent dye of formula II has the formula

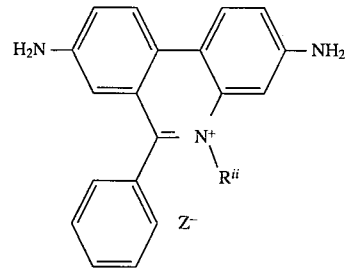

wherein $R^{ii}$ is a $C_6$ alkyl;

where the dye of formula III has the formula:

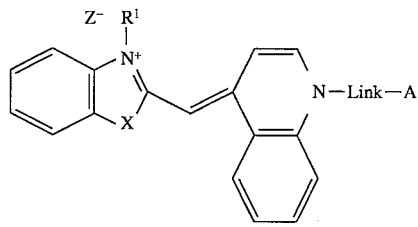

wherein

X is O or S; and $R^1$ is an alkyl group of 1–2 carbons;

LINK is an aliphatic chain containing a backbone of 4 to 19 methylene groups (—$CH_2$—), optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or $CH_3$, LINK must contain at least one N heteroatom;

A is H, CH₃ or is

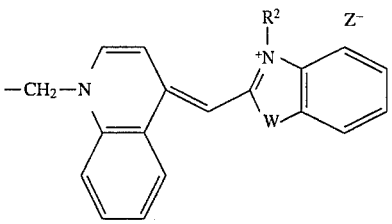

wherein

W is O or S;

R² is an alkyl group of 1–2 carbons; and where the fluorescent dye IV is a lectin that binds selectively to N-acetylglucosamine and is covalently bound to a blue fluorescent fluorophore;

and step c) further comprises illuminating the dyed bacteria mixture at a wavelength between about 480 nm and about 510 nm.

12. A method as in claim 11 wherein said bacteria sample is combined with an aqueous dye solution comprising a fluorescent dye of formula I in combination with an aqueous dye solution comprising a fluorescent dye of formula II, where the fluorescent dye of formula I stains intracellular nucleic acids for all bacteria in the sample and the fluorescent dye of formula II stains intracellular nucleic acids for all Gram positive bacteria in the sample.

13. A method, as claimed in claim 5, wherein for said dye of formula II, $R^{ii}$ is $C_6$–$C_8$ alkyl.

14. A method, as claimed in claim 5, wherein said dye of formula III has the formula:

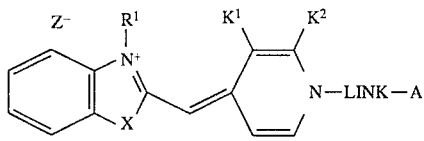

wherein

X is O or S;

R¹ is an alkyl group of 1–2 carbons;

K¹ and K² may be the same or different, and are independently hydrogen, an alkyl group having 1–6 carbons, or aryl; or K¹ and K² taken in combination complete a 6-membered aromatic ring;

LINK is an aliphatic chain containing a backbone of 4 to 19 methylene groups (—CH₂—), optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or CH₃, LINK must contain at least one N heteroatom;

A is H, CH₃ or is

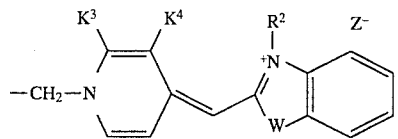

wherein

W is O or S;

R² is an alkyl group of 1–2 carbons; and

K³ and K⁴ may be the same or different, and are independently hydrogen, an alkyl group having 1–6 carbons, or aryl; or K³ and K⁴ taken in combination complete a 6-membered aromatic ring.

15. A method of analyzing bacteria for Gram reaction and viability, comprising:

a) combining a bacteria sample, simultaneously or sequentially, with an aqueous dye solution comprising a fluorescent dye of formula III, in combination with an aqueous dye solution comprising a fluorescent dye of formula II or an aqueous dye solution comprising a fluorescent dye IV or both, where each dye is present in solution in an amount sufficient to give a detectable fluorescent response and where each dye present in solution is selected such that its detectable fluorescent response, after staining and illumination of the sample, is different from the fluorescent response of any other dye being combined;

wherein said dye of formula II has the formula

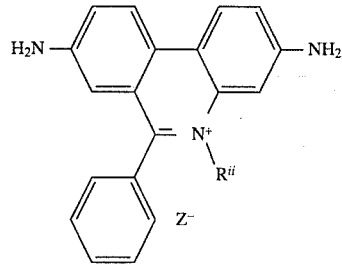

wherein $R^{ii}$ is a $C_4$–$C_8$ alkyl: and Z⁻ is a biologically compatible counterion;

said dye of formula III has the formula

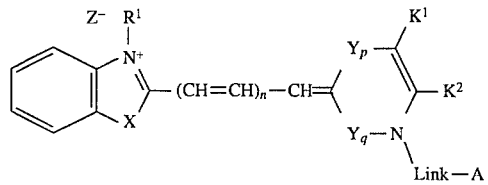

wherein

X is O, S, Se, or C(CH₃); and

R¹ is an alkyl group of 1–6 carbons;

n=0, 1 or 2;

Y is —CH₂=CH₂—;

p and q are equal to 0 or 1, such that p+q=1;

K¹ and K² may be the same or different, and are independently hydrogen, an alkyl group having 1–6 carbons, or aryl; or K¹ and K² taken in combination complete a 6-membered aromatic ring;

LINK is an aliphatic chain containing a backbone of 4 to 19 methylene groups (—CH₂—), optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or $CH_3$, LINK must contain at least one N heteroatom;

A is H, $CH_3$ or is

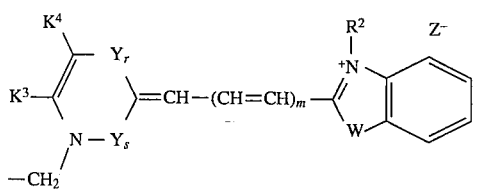

wherein

W is O, S, Se, or $C(CH_3)$;

$R^2$ is an alkyl group of 1–6 carbons:

m=0, 1 or 2;

Y is $-CH_2=CH_2-$;

r and s equal to 0 or 1, such that r+s=1;

$K^3$ and $K^4$ may be the same or different, and are independently hydrogen, an alkyl group having 1–6 carbons, or aryl; or $K^3$ and $K^4$ taken in combination complete a 6-membered aromatic ring;

said dye IV is a fluorescent reagent that preferentially binds to an exterior component of Gram-positive bacterium;

b) allowing sufficient time for each dye in solution to combine with one or more bacterium in the sample to give a dyed bacteria mixture;

c) illuminating the dyed bacteria mixture at a suitable absorption wavelength that results in one or more illuminated bacterium;

d) observing the illuminated bacterium with means for detecting the fluorescent response resulting from illumination; and e) analyzing the fluorescent response of said illuminated bacterium, wherein the fluorescent dye of formula II stains intracellular nucleic acids for all Gram positive bacteria in the sample:

the fluorescent dye of formula III stains the nucleic acids for all dead bacteria in the sample; and the fluorescent dye IV stains the external surface of all Gram positive bacteria in the sample.

16. A method as in claim 15; wherein step a) further comprises combining a bacteria sample, simultaneously or sequentially, with an aqueous dye solution comprising a fluorescent dye of formula III, in combination with an aqueous dye solution comprising a fluorescent dye of formula II or an aqueous dye solution comprising a fluorescent dye IV or both, and further comprising an aqueous solution comprising a fluorescent dye of formula I, where each dye present in solution is present in a concentration between about 1 μM and about 30 μM, where the fluorescent dye of formula I has the formula:

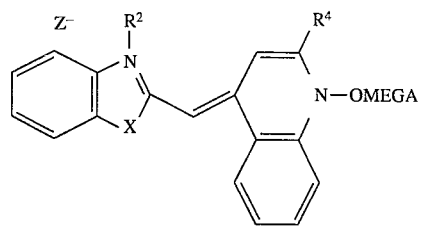

wherein $R^2$ is methyl or ethyl;

X is O or S;

$R^4$ is H, alkyl, alkenyl, polyalkenyl, alkynyl or polyalkynyl having 1–6 carbons; or a halogen; or $-OR^8$, $-SR^8$, $-(NR^8R^9)$; or $-OSO_2R^{19}$;

OMEGA is phenyl or cyclohexyl; and $Z^-$ is a biologically compatible ion;

where the fluorescent dye of formula II has the formula

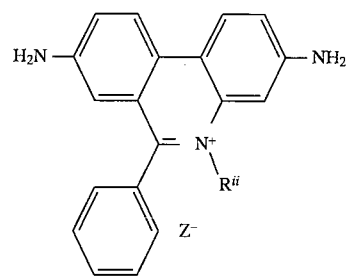

wherein $R^{ii}$ is a $C_6$ alkyl;

where the dye of formula III has the formula:

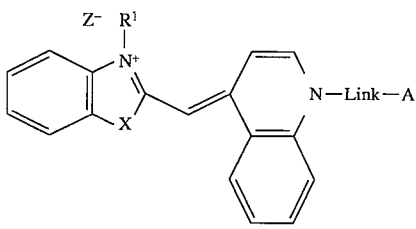

wherein

X is O or S; and $R^1$ is an alkyl group of 1–2 carbons;

LINK is an aliphatic chain containing a backbone of 4 to 19 methylene groups ($-CH_2-$), optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or $CH_3$, LINK must contain at least one N heteroatom;

A is H, CH₃ or is

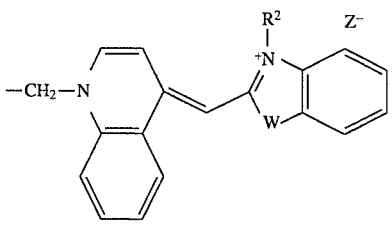

wherein

W is O or S;

R² is an alkyl group of 1–2 carbons; and where the fluorescent dye IV is a lectin that binds selectively to N-acetylglucosamine and is covalently bound to a blue fluorescent fluorophore; and where the aqueous dye solution comprising a fluorescent dye of formula IV further comprises an amount of albumin in a concentration greater than 0 and less than about 5 percent; and where each dye present in solution is selected such that its detectable fluorescent response, after staining and illumination of the sample, is different from the fluorescent response of any other dye in the solution;

and step c) further comprises illuminating the dyed bacteria mixture at a wavelength between about 480 nm and about 5 10 nm.

17. A method as in claim 16 where the bacteria sample contains bacteria, which may be the same or different, selected from the group consisting of *Bacillus cereus, Bacillus subtilis, Clostridium sporogenes, Corynebacterium xerosis, Micrococcus luteus, Mycobacterium phlei, Propionibacterium freudenreichii, Staphylococcus aureus, Streptococcus pyogenes, Lactobacillus acidophilus, Cytophaga psychrophila, Enterobacter aerogenes, Escherichia coli, Flavobacterium meningosepticum, Klebsiella pneumoniae, Neisseria subflava, Pseudomonas aeruginosa, Rhizobium trifolii, Salmonella oranienburg, Shigella sonnei,* and *Vibrio parahaemolyticus.*

18. A method as in claim 15 further comprising combining said sample with an aqueous dye solution comprising a fluorescent dye IV that is a surface label that is a protein conjugate that is specific to a particular genus or species or serotype of bacterium.

19. A method as in claim 15, where the fluorescent dye of formula II stains intracellular nucleic acids for all Gram positive and dead Gram negative bacteria; the fluorescent dye of formula III stains intracellular nucleic acids for all dead bacteria; and the fluorescent dye IV binds selectively to the surface of Gram positive bacteria and further comprises an aqueous solution of a fluorescent dye of formula I that stains intracellular nucleic acids for all bacteria, where each dye is present in solution in an amount sufficient to give a detectable fluorescent response and where each dye present in solution is selected such that its detectable fluorescent response, after staining and illumination of the sample, is different from the fluorescent response of any other dye being combined wherein said dye of formula I has the formula

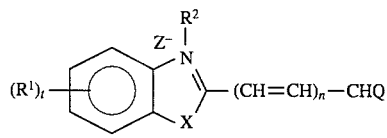

wherein each R¹ is independently H; or an alkyl group having from 1–6 carbons; or a trifluoromethyl; or a halogen; or —OR⁸, —SR⁸ or —(NR⁸R⁹) where R⁸ and R⁹, which can be the same or different, are independently H; or alkyl groups having 1–6 carbons; or 1–2 alicyclic, heteroalicyclic, aromatic or heteroaromatic rings, containing 1–4 heteroatoms, wherein the hetero atoms are O, N or S; or R⁸ and R⁹ taken in combination are —(CH₂)₂—L—(CH₂)₂— where L=a single bond, —O—, —CH₂—, or —NR¹⁰— where R¹⁰ is H or an alkyl group having 1–6 carbons; and t=1–4;

R² is an alkyl group having 1–6 carbons;

X is O, S, Se or NR¹⁵, where R¹⁵ is H or an alkyl group having 1–6 carbons; or X is CR¹⁶R¹⁷ where R¹⁶ and R¹⁷, which may be the same or different, are independently alkyl groups having 1–6 carbons, or R¹⁶ and R¹⁷ taken in combination complete a five or six membered saturated ring:

n=0, 1 or 2;

Z⁻ is a biologically compatible counterion:

Q has the formula Q1 or Q2

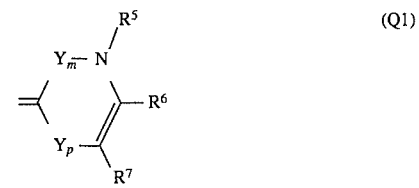

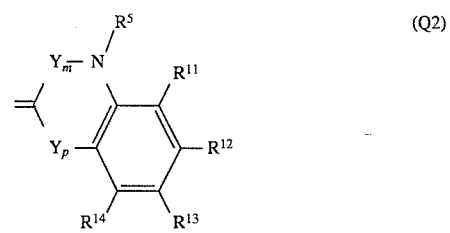

wherein

Y is —CR³=CR⁴—;

p and m=0 or 1, such that p+m=1;

R⁵ is an alkyl, alkenyl, polyalkenyl, alkynyl or polyalkynyl group having 1–6 carbons; or R⁵ is an OMEGA;

R³, R⁴, R⁶ and R⁷, which may be the same or different are independently H: or an alkyl, alkenyl, polyalkenyl, alkynyl or polyalkynyl group having 1–6 carbons; or a halogen; or —OH, —OR⁸, —SR⁸, —(NR⁸R⁹); or —OSO₂R¹⁹ where R¹⁹ is alkyl having 1–6 carbons, or perfluoroalkyl having 1–6 carbons, or aryl; or an OMEGA;

or R⁶ and R⁷, taken in combination are —(CH₂)ᵥ— where v=3 or 4, or R⁶ and R⁷ form a fused aromatic ring according to formula Q2:

R¹¹, R¹², R¹³, and R¹⁴, which may be the same or different, are independently H; or an alkyl, alkenyl, polyalkenyl, alkynyl or polyalkynyl group having 1–6 carbons; or a halogen; or an OMEGA; or —OH, —OR⁸, —SR⁸, or —(NR⁸R⁹);

OMEGA is a saturated or unsaturated, substituted or unsubstituted cyclic substituent that has a total of 2–16 ring carbon atoms in 1–2 alicyclic, heteroalicyclic, aromatic, or heteroaromatic rings, containing 1–4 heteroatoms wherein the hetero atoms are O, N or S, that is unsubstituted or optionally substituted one or more times, independently, by halogen, alkyl, perfluoroalkyl, alkoxy or carboxyalkyl, having 1–6 carbons, and that is attached as $R^3$, $R^4$, $R^5$, $R^6$, $R^7$, $R^{11}$, $R^{12}$, $R^{13}$, or $R^{14}$ by a single bond:

such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different.

20. A method as in claim 19, wherein the fluorescent dye of formula I has the structure:

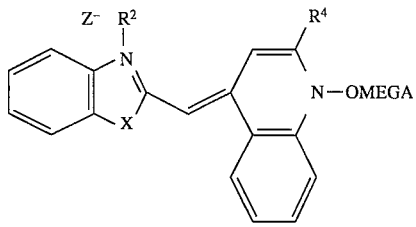

wherein
$R^2$ is methyl or ethyl;
X is O or S;
$R^4$ is H, alkyl, alkenyl, polyalkenyl, alkynyl or polyalkynyl having 1–6 carbons; or a halogen; or —$OR^8$, —$SR^8$, —($NR^8R^9$); or —$OSO_2R^{19}$;
OMEGA is phenyl or cyclohexyl; and
$Z^-$ is a biologically compatible ion;
where the fluorescent dye of formula II has the formula

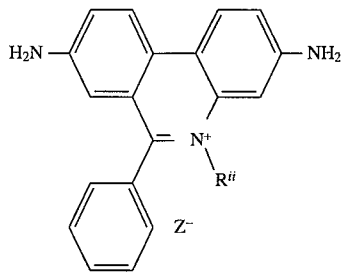

wherein $R^{ii}$ is a $C_6$ alkyl;

the fluorescent dye of formula III has the structure:

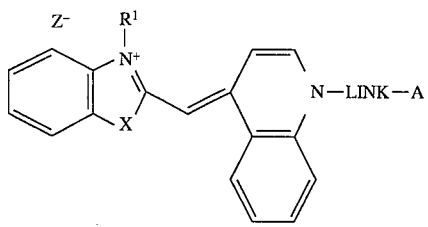

wherein
X is O or S; and
$R^1$ is an alkyl group of 1–2 carbons;
LINK is an aliphatic chain containing a backbone of 4 to 19 methylene groups (—$CH_2$—), optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or $CH_3$, LINK must contain at least one N heteroatom;
A is H, $CH_3$ or is

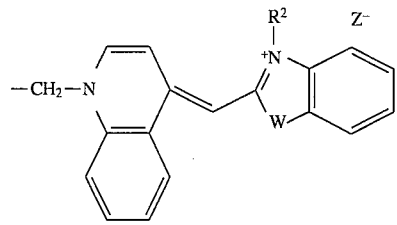

wherein
W is O or S; and
$R^2$ is an alkyl group of 1–2 carbons.

* * * * *

UNITED STATES PATENT AND TRADEMARK OFFICE
CERTIFICATE OF CORRECTION

PATENT NO. : 5,545,535
DATED : August 13, 1996
INVENTOR(S) : Roth, et al.

It is certified that error appears in the above-indentified patent and that said Letters Patent is hereby corrected as shown below:

col 1, line 20, "frown" should be --from--.

col 7, line 59, "$R^1$ is" should be --$R^1$ that is--.

col 22, line 29, "*lute us*" should be --*luteus*--.

col 23, line 28, "$R^{16}$ $R^{17}$" should be --$R^{16}$ and $R^{17}$--.

col 40, line 57, "single O bond" should be --single bond--.

Signed and Sealed this

Ninth Day of September, 1997

Attest:

BRUCE LEHMAN

Attesting Officer

Commissioner of Patents and Trademarks